(12) United States Patent
Kochkine et al.

(10) Patent No.: US 6,734,291 B2
(45) Date of Patent: *May 11, 2004

(54) SYNTHESIS OF [2.2.1]BICYCLO NUCLEOSIDES

(75) Inventors: Alexei Kochkine, København (DK); Jef Fensholdt, Søborg (DK); Henrik M. Pfundheller, Frederiksberg (DK)

(73) Assignee: Exiqon A/S (DK)

(*) Notice: Subject to any disclaimer, the term of this patent is extended or adjusted under 35 U.S.C. 154(b) by 0 days.

This patent is subject to a terminal disclaimer.

(21) Appl. No.: 10/233,177

(22) Filed: Dec. 16, 2002

(65) Prior Publication Data

US 2003/0092905 A1 May 15, 2003

Related U.S. Application Data

(63) Continuation of application No. 09/534,769, filed on Mar. 24, 2000, now Pat. No. 6,639,059.
(60) Provisional application No. 60/127,355, filed on Apr. 1, 1999, and provisional application No. 60/178,518, filed on Jan. 24, 2000.

(30) Foreign Application Priority Data

Mar. 24, 1999 (DK) .......................... 1999 00407
Jan. 21, 2000 (DK) .......................... 2000 00099

(51) Int. Cl.$^7$ .......................................... C07H 15/04
(52) U.S. Cl. ........................................ 536/4.1; 536/18.6
(58) Field of Search ............................ 536/4.1, 18.6

(56) References Cited

U.S. PATENT DOCUMENTS 6,043,060 A * 3/2000 Imanishi .................... 435/91.1
6,639,059 B1 * 10/2003 Kochkine et al. ............ 536/4.1

FOREIGN PATENT DOCUMENTS

| EP | 0538194 B1 | 4/1999 |
| EP | 1 013 661 A1 * | 6/2000 |
| JP | 06-080688 A2 * | 3/1994 |
| WO | WO98/22489 | 5/1998 |
| WO | WO98/39352 | 9/1998 |
| WO | WO99/14226 | 3/1999 |
| WO | WO 00/56746 A2 * | 9/2000 |
| WO | WO 00/56748 A1 * | 9/2000 |
| WO | WO 00/66604 A2 * | 11/2000 |
| WO | WO 00/78775 A2 * | 12/2000 |

OTHER PUBLICATIONS

Rajwanshi et al., "Synthesis and Restricted Furanose Conformations of Three Novel Bicyclic Thymine Nucleosides: a Xylo– LNA Nucleoside, a 3'–O, 5'–C– Methylene–linked Nucleoside, and a 2'–O, 5'–C– Methylene–linked Nuclesode," *J. Chemical Society, Perkin Transactions I,* (Issue No. 11), 1407–1414 (Jun. 7, 1999).*

Waga et al., "Synthesis of 4'–C– Methylnucleosides," *Bioscience, Biotechnology, and Biochemistry,* 57(9), 1433–1438 (Sep., 1993).*
Youssefyeh et al., "Synthetic Routes to 4'–Hydroxymethylnucleosides," *Tetrahedron Letters,* (Issue No. 5), 435–438 (Jan., 1977).*
Tarkoy et al., *Helv. Chim. Acta,* 76:481 (1993).
Tarkoy et al., *Angew. Chem., Int. Ed. Engl.,* 32:1432 (1993).
Egli et al., *J. Am. Chem. Soc.,* 115:5855 (1993).
Tarkoy et al., *Helv. Chim. Acta,* 77:716 (1994).
Bolli et al., *Angew. Chem., Int. Ed. Engl.,* 34:694 (1995).
Bolli et al., *Helv. Chim. Acta,* 78:2077 (1995).
Litten et al., *Bioorg. Med. Chem. Lett.,* 5:1231 (1995).
Litten et al., *Helv. Chim. Acta,* 79:1129 (1996).
Bolli et al., *Chem. Biol.,* 3:197 (1996).
Bolli et al., *Nucleic Acids. Res.,* 24:4660 (1996).
K.H. Altmann et al., *Tetrahedron Lett.,* 35::2331 (1994)
K.H. Altmann et al., *Tetrahedron Lett.,* 35:7625 (1994).
Marquez et al., *J. Med. Chem.,* 39:3739 (1996).

(List continued on next page.)

*Primary Examiner*—James O. Wilson
*Assistant Examiner*—Lawrence E Crane
(74) *Attorney, Agent, or Firm*—Peter F. Corless; Christine C. O'Day; Edwards & Angell, LLP

(57) ABSTRACT

A synthesis of [2.2.1]bicyclo nucleosides which is shorter and provides higher overall yields proceeds via the key intermediate of the general formula III, wherein $R_4$ and $R_5$ are, for instance, sulfonates and $R_7$ is, for instance, a halogen or an acetate. From compounds of the general formula II, such as 3-O-aryl-4-C-hydroxymethyl-1,2-O-isopropylidene-α-D-ribofuranose, intermediates of the general formula III are suitable for coupling with silylated nucleobases. Upon one-pot base-induced ring-closure and desulfonation of the formed [2.2.1]bicyclo nucleoside, a short route to each the LNA (Locked Nucleic Acid) derivatives of adenosine, cytosine, uridine, thymidine and guanidine is demonstrated. The use of the 5'-sulfonated ring-closed intermediate also allows for synthesis of 5'-amino- and thio-LNAs

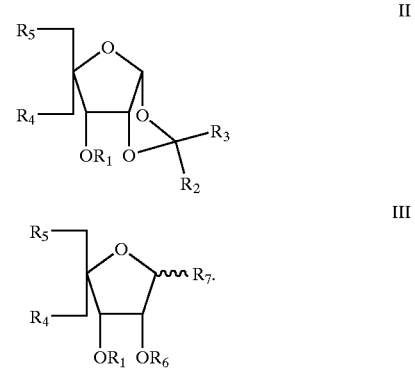

15 Claims, 8 Drawing Sheets

OTHER PUBLICATIONS

Figure 1:
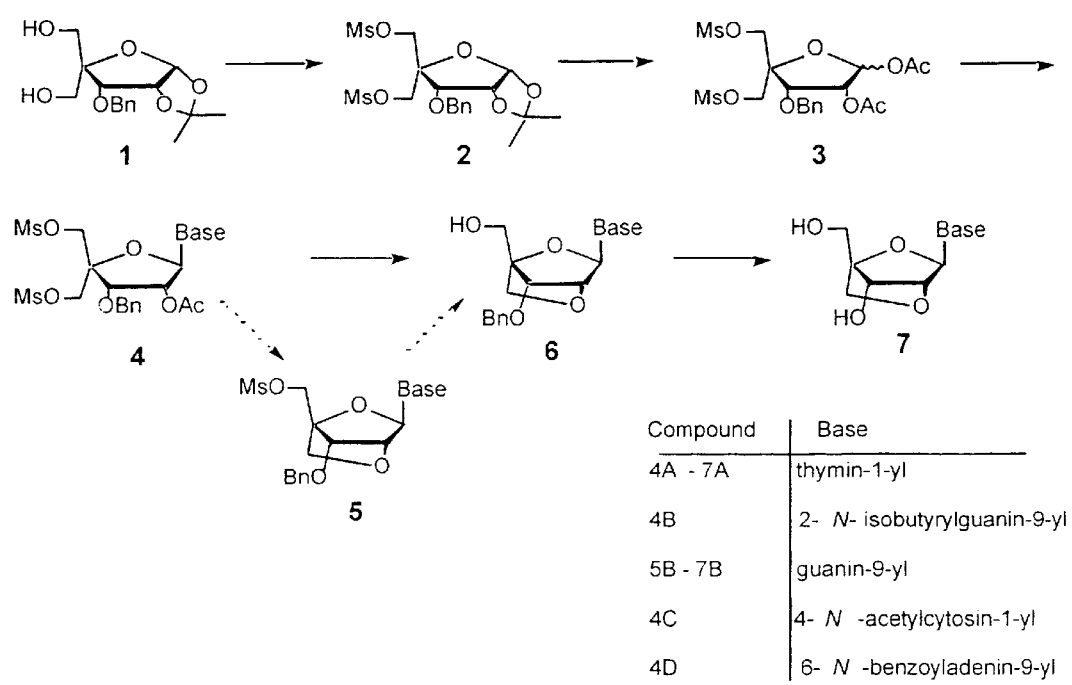

Ezzitouni et al., *J. Chem. Soc., Perkin Trans.,* 1:1073 (1997).
Jones et al., *J. Am. Chem. Soc.,* 115:9816 (1993).
Wang et al., *Bioorg. Med. Chem. Lett.,* 7:229 (1997).
Yannopoulus et al., *Synlett,* 378(1997). (Apr., 1997).
CHIMA, 36th IUPAC Congress, organized by the Swiss Chemical Society. Poster No.SB–B4: Steffens, R. and Leumann Ch. Tricyclo–DNA: synthesis, enzymatic stability, and pairing properties. (Aug. 18, 1997).
Nielsen, Master Thesis (Odense University, Denmark), pp. 67–71 (1995). (Jan. 1995).
Youssefyeh et al., *J. Org. Chem.,* 44:1301 (1979).
Jones et al., *J. Org. Chem.,* 44:1309 (1979).
Yang et al., *Tetrahedron Lett.,* 33:37 (1992).
Thrane et al., *Tetrahedron,* 51:10389 (1995).
Nielsen et al., *Bioorg. Med. Chem.,* 3:1493 (1995).
Freier et al., *Nucleic Acid Research,* 25:4429–4443 (1997).
Haly et al., *Synlett,* 687–689 (1996).
Zou et al., *Tetrahedron Lett.,* 37:941–944 (1996).
Herdewijn., *Liebigs Ann.,* 1137–1348 (1996).
Obika et al., *Tetrahedron Lett.,* 39:5401–5404 (1998).
Obika et al., *Tetrahedron Lett.,* 38:8735–8738 (1997).
7th Antisense Symposium, Nov. 21–22, 1997. Poster No. 32 and 33: Obika, D.N.; Morio, K. and Imanishi, T. Synthesis and properties of oligonucleotides containing novel bicyclic nucleosides with a fixed N–form sugar puckering.
Chima, 36th IUPAC Congress, organized by the Swiss Chemical Society. Poster No. SB–B12: Egtger, A. and Leumann Ch. Designe, synthesis and properties of bicyclo [3.2.1]–amino nucleic acids. (Aug. 18, 1997).
Chima, 36th IUPAC Congress, organized by the Swiss Chemical Society. Poster No SB–B5: Epple, C. Ch., Pompizi, I. and Leumann Ch. Bicyclo [3.2.1]–DNA: an oligonucleotide analogue with a conformationally preorganized Phosphodiester backbone and a flexible sugar–base linkage. (Aug. 18, 1997).
Sep. 6–10, 1998: 13th International Round Table—Nucleoside, Nucleotides and their Biological Applications, Montpeilleir: Oral Communication 1: Wang, G. and Gunic, E. "Conformationally Locked Nucleoside Analogs. Synthesis of 2'–Deoxy–2'–C, 4'–C–Bridged Bicyclic Nucleoside".
Sep. 6–10, 1998: 13th International Round Table—Nucleoside, Nucleotides and their Biological Applications, Montpeilleir: Poster No. 288: Meldgaard, M. et al., "LNA (Locked Nucleic Acids): Synthesis and Thermal Denaturation Studies".
Sep. 6–10, 1998: 13th International Round Table—Nucleoside, Nucleotides and their Biological Applications, Montpeilleir: Poster No. 287 and Proceeding: Koshkin, A. A. et al., "Locked Nucleic Acids as synthetic RNA Mimics for Effective Complmentary Recognition".
Sep. 6–10, 1998: 13th International Round Table—Nucleoside, Nucleotides and their Biological Applications, Montpeilleir: Poster No. 67: Nielsen, P. and Wengel, J. "A New Covergent Synthetic Approach Towards a–and β–LNA (Locked Nucleic Acids)".
Oct. 8, 1998: Antisense 98, Targeting the Molecularl Basis of Disease: Poster No. 24: Havsteen, M. et al., "LNA (Locked Nucleic Acids): A new Class of High Affinity Nucleic Acids With Prime Potential as Antisense and Antigene Agents".
Jan. 21, 1998: National Seminar on Perspectives in Interfacial Areas of Chemistry and Biology, Delhi University: Wengel, J. "LNA (Locked Nucleic Acids): Synthesis and High Affinity Nucleic Acid Recognition—Stop the Twisting".
27 Marts 1998: Workshop of Young European Bioorganic Chemists, Munchen: Wengel, J. "LNA (Locked Nucleic Acids): Synthesis and High Affinity Nucleic Acid Recognition—Stop the Twisting".
Aug. 20, 1998: Årsmødet for Center for Medicinski Bioteknologi, KVL: Wengel, J. "LNA (Locked Nucleic Acids)"ations, Montpeiller: Oral Communication 1: Wang, G. and Gunic, E. "Conformationally Locked Nucleoside Analogs, Synthesis of 2'–Deoxy–2'–C, 4'–C–Bridged Bicyclic Nucleoside".
Sep. 7, 1998: 13th International Round Table—Nucleoside, Nucleotides and their Biological Applications, Montpeilleir: Oral Communication 2: Wengel, J. "LNA (Locked Nucleic Acids".
Sep. 8, 1998: Meeting in Lund, Sweden: Jakobsen, M. H. "LNA (Locked Nucleic Acids): A new Class of High Affinity Nucleic Acids With Prime Potential as Antisense and Antigene Agents".
Nielsen et al., *J. Chem. Soc., Perkin Trans.,* 1:3423–3433 (1997). (Perkin Trans. I).
Nielsen et al., *Chem. Commun.,* 9:825–826 (1997).
Singh et al., *Chem. Commun.,* 455–456 (1998).
Koshkin et al., *Tetrahedron,* 54:36073630 (1998).
Koshkin et al., *Tetrahedron Lett.,* 39:4381–8384 (1998).
Singh et al., *Chem. Commun.,* 1237–1248 (1998).
Singh et al., *J. Org. Chem.,* 63:6078–6079 (1998).
Christensen et al., *J. Am. Chem. Soc.,* 120:5458–5463 (1998).
Koshkin et al., *J. Org. Chem.,* 63:2778–2781 (1998).
Kumar et al., *Bioorg. Med. Chem. Lett.,* 8:2219–2222 (1998).
Wengel et al., *Acc. Chem. Res.,* 32:301–310 (1999).
Koshkin et al., *J. Am. Chem. Soc.,* 120:13252–13253 (1998).
Singh et al., *J. Org. Chem.,* 10035–10039 (1998).
Nielsen et al., *Chem. Commun.,* 2645–2646 (1998).
Wengel et al., *Nucleosides Nucleoties,* 18:1365–1370 (1999).
Nielsen et al., *Nucleosides Nucleotides,* 18:701–702 (1999).
Kaerno et al., *Chem. Commun.,* 657–658 (1999).
Rajwanshi et al., *J. Chem. Soc., Perkin Trans.,* 1:1407–1414 (1999). (Perkin Trans. I).
Raunkjaer et al., *J. Chem. Soc., Perkin Trans.,* 1:2543–2551 (1999). (Perkin Trans I).
Rajwanshi et al., *Chem. Commun.,* 1395–1396 (1999).
Pfundheller et al., *Nucleosides Nucleotides,* 18:2017–2030 (1999).
Rajwanshi et al., *Chem. Commun.,* 2073–2074 (1999).
Nielsen et al., *J. Biomol. Struc. Dyn.,* 17:175–191 (1999).
Nielsen et al., *Bioconjugate Chem.,* 11:228–238 (2000).
Rajwanshi et al., *Angewandte Chemie,* 39:1656–1659 (2000).
Minasov et al., *Biochemistry,* 39:3525 (2000).
Wahlesttedt et al., *Proc. Natl. Acad. Sci. USA.* 97:5633–5638 (2000). (May 9, 2000).
Obika et al., *Tetrahedron Lett.,* 40:6465–6468 (1999).
Obika et al., *Tetrahedron Lett.,* 41:215–219 (1999).
Obika et al., *J. Chem. Soc., Chem. Commun.,* 2423–2424 (1999).

Wang et al., *Bioorg. Med. Chem. Lett.*, 9:1147–1150 (1999).
Obika et al., *Tetrahedron Lett.*, 41:221–224 (1999).
Obika et al., *Bioorg. Med. Chem. Lett.*, 9:515–518 (1999).
Obika et al., *Tetrahedron Lett.*, 39:5401–5405 (1998).
Imanishi et al., *J. Synth. Org. Chem.*, 57:959–980 (1999). (J. Synth. Org. Chem. Japan).

Chemical Abstracts, vol. 70, No. 1, Abstract No. 3737B (1969).
*Monatsch. Chem.*, 99(5):2111–2120 (1968).
Tam et al., *Can. J. Chem.*, 57:2818–2822 (1979).

* cited by examiner

| Compound | Base |
|---|---|
| 4A - 7A | thymin-1-yl |
| 4B | 2-N-isobutyrylguanin-9-yl |
| 5B - 7B | guanin-9-yl |
| 4C | 4-N-acetylcytosin-1-yl |
| 4D | 6-N-benzoyladenin-9-yl |

SYNTHESIS OF [2.2.1]BICYCLO NUCLEOSIDES

This application is a continuation of Ser. No. 09/534,769 filed Mar. 24, 2000, and claims provision of Ser. No. 60/127,355 filed Apr. 1, 1999, and Ser. No. 60/178,518 filed Jan. 24, 2000.

FIELD OF THE INVENTION

The present invention relates to a new strategy for the synthesis of [2.2.1]bicyclo nucleosides which is shorter, provides higher overall yields, and thus more cost efficient than previously known methods for synthesis of [2.2.1] bicyclo nucleosides.

BACKGROUND OF THE INVENTION

Synthesis of the LNA (Locked Nucleic Acid) monomer (1S, 3R, 4R, 7S)-7-hydroxy-1-hydroxymethyl-2,5-dioxabicyclo[2.2.1]heptane uracil was first reported by Obika. (Satashi Obika et al., *Tetrahedron Lett.*; 1997; 8735–8738) who used a linear strategy based on uridine as starting material for the synthesis of the intermediate 1-(3-O-benzyl-4-C-tosyloxymethyl-β-D-ribofuranosyl)uridine. Treatment of the tosylated nucleoside intermediate with sodium hexamethyidisilazide in THF afforded the 2'-O, 4'-C-methylene bicyclonucleoside which upon final debenzylation afforded (1S, 3R, 4R, 7S)-7-hydroxy-1-hydroxymethyl-2,5-dioxabicyclo[2.2.1]heptane uracil in 36% yield from the tosylated nucleoside intermediate.

Wengel et al. (Singh, S. K.; Nielsen, P., Koshkin, A. A. and Wengel, J., *Chem. Commun.*, 1998, 455; Koshkin, A. A.; Singh, S. K.; Nielsen, P.; Rajwanshi, V. K.; Kumar, R; Melgaard, M.; Olsen, C. E. and Wengel, J., *Tetrahedron*, 1998, 54, 3607) subsequently reported on a convergent strategy for the synthesis of the thymine analogue (1S, 3R, 4R, 7S)-7-hydroxy-1-hydroxymethyl-(thymin-1-yl)-2,5-dioxabicyclo[2.2.1]heptane. Starting from 3-O-benzyl-4-C-hydroxymethyl-1,2-O-isopropylidene-α-D-ribofuranose, the key intermediate for coupling with silylated thymine (or other silylated nucleobases), 4-C-acetoxymethyl-1,2-di-O-acetyl-3,5-di-O-benzyl-D-ribofuranose, was obtained by successive regioselective 5-O-benzylation, acetylation, acetolysis, and another acetylation. Coupling of the key intermediate with silylated thymine afforded the 4'-C-acetoxymethyl nucleoside which upon deacetylation and monotosylation followed by base-induced ring closure, afforded the 2'-O, 4'-C-methylene bicyclonucleoside. Final debenzylation gives (1S, 3R, 4R, 7S)-7-hydroxy-1-hydroxymethyl-(thymin-1-yl)-2,5-dioxabicyclo[2.2.1] heptane in 40% yield (calculated from the key intermediate). Analogous synthetic procedure were applied for the synthesis of the uracil, 2-N-isobutyrylguanine, 4-N-benzoylcytosine and 6-N-benzoylcytosine LNA nucleoside analogues. The corresponding 2'-amino-LNA pyrimidine nucleosides were obtained by performing the ring closure in benzylamine. Debenzylation and subsequently silylation using 1,3-dichloro-1,1,3,3-tetraisopropyidisiloxane afforded a bicyclic intermediate which was easily converted into the 2'-thio-LNA analogue upon reaction with potassium thioacetate in DMF and final desilylation (Singh, S. K.; Kumar, R. and Wengel, J., *J. Org. Chem.*, 1998, 63, 6078).

An analogous convergent synthesis of the (1S, 3R, 4R, 7S) -7-hydroxy-1-hydroxymethyl-2,5-dioxabicyclo[2.2.1] heptane thymine using 4-C-tosyloxymethyl-1,2-di-O-acetyl-3,5-di-O-benzyl-D-ribofuranose as the key intermediate for coupling with silylated nucleobases has been reported by the same group (Koshkin, A. A., Rajwanshi, V. K., and Wengel J., *Tetrahedron Lett.*, 1998, 39, 4381).

The use of a 4-C-tosyloxymethyl ribofuranose intermediate has also been suggested by Obika, S. et al (WO 98/39352). In this strategy the 5-O-benzyl protecting group is exchanged for a tert-butyidimethylsilyl protecting group thereby extending the total synthesis of (1S, 3R, 4R, 7S)-7-hydroxy-1-hydroxymethyl-2,5-dioxabicyclo[2.2.1] heptane nucleosides with one step.

Characteristic properties of the previously known strategies discussed above are relatively low overall yields and many synthetic steps. Thus, there is a great need for development of a more efficient synthesis strategy which will result in an improvement of the overall yield and a reduction in the production costs of [2.2.1]bicyclo nucleosides.

SUMMARY OF THE INVENTION

The present invention provides a novel strategy for the synthesis of [2.2.1]bicyclic nucleosides comprising the synthesis of a novel key intermediate. The novel strategy is demonstrated by the synthesis of (1S, 3R, 4R, 7S)-7-hydroxy-1-hydroxymethyl-(thymin-1-yl)-2,5-dioxabicyclo [2.2.1]heptane and has easily been extended to the synthesis of [2.2.1]bicyclo nucleosides containing other nucleobases and can be further extended to other heteroatoms than oxygen in the bicycle, such as amino and thio.

The present invention relates to a method for the synthesis of a novel intermediate of the general formula II:

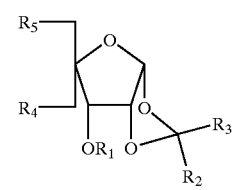

II wherein $R_1$ is selected form optionally substituted aryl($C_{1-6}$-alkyl), optionally substituted tetrahydropyran-2-yl, optionally substituted arylcarbonyl and optionally substituted aryl;

each of the substituents $R_2$ and $R_3$ is independently selected from hydrogen, optionally substituted $C_{1-6}$-alkyl, optionally substituted aryl, and optionally substituted aryl($C_{1-6}$-alkyl), with the proviso that $R_2$ and $R_3$ are not both hydrogen, or $R_2$ and $R_3$ together designate $C_{3-7}$-alkylene; and each of the substituents $R_4$ and $R_5$ independently is R'SO$_2$O— wherein R' is selected from optionally substituted alkyl and optionally substituted aryl;

said method comprising the following step:
treatment of a compound (hereinafter termed "starting material") of the general formula I:

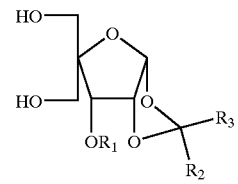

I wherein $R_1$ is selected form optionally substituted aryl($C_{1-6}$-alkyl), optionally substituted tetrahydropyran-2-yl, optionally substituted arylcarbonyl and optionally substituted aryl;

each of the substituents $R_2$ and $R_3$ is independently selected from hydrogen, optionally substituted $C_{1-6}$-alkyl, optionally substituted aryl, and optionally substituted aryl($C_{1-6}$-alkyl), with the proviso that $R_2$ and $R_3$ are not both hydrogen, or $R_2$ and $R_3$ together designate $C_{3-7}$-alkylene; and with R'SO$_2$X wherein R' is selected from optionally substituted $C_{1-6}$-alkyl and optionally substituted aryl, and X designates halogen.

The present invention also relates to the compound of the general formula II as defined above.

The present invention furthermore relates to the compound (hereinafter termed "key intermediate") of the general formula III:

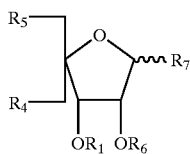

III wherein $R_1$ is selected form optionally substituted aryl($C_{1-6}$-alkyl), optionally substituted tetrahydropyran-2-yl, optionally substituted arylcarbonyl and optionally substituted aryl;

each of the substituents $R_4$ and $R_5$ independently is R'SO$_2$O— wherein R' is selected from optionally substituted alkyl and optionally substituted aryl;

$R_6$ is selected from hydrogen, optionally substituted ($C_{1-6}$-alkyl)carbonyl, optionally substituted arylcarbonyl, optionally substituted aryl($C_{1-6}$-alkyl), optionally substituted $C_{1-6}$-alkyl, and tri(alkyl/aryl)silyl; and $R_7$ is selected from optionally substituted ($C_{1-6}$-alkyl)carbonyloxy, optionally substituted $C_{1-6}$-alkoxy, halogen, optionally substituted arylthio, optionally substituted $C_{1-6}$-alkylthio, and optionally substituted aryloxy.

The main advantages of the present invention comprise the following:

Obtaining the key intermediate of the general formula III ready for coupling with silylated nucleobases in very few steps from 3-O-benzyl-4-C-hydroxymethyl-1,2-O-isopropylidene-α-D-ribofuranose.

One-pot base-induced ring-closure and desulfonation of the formed [2.2.1]bicyclo nucleoside.

The possibility of using the 5'-sulfonated ring-closed intermediate (compound 5a in example 4) for synthesis of 5'-amino- and thio-LNA.

DETAILED DESCRIPTION OF THE INVENTION

In an attempt to improve the synthesis of [2.2.1]bicyclo nucleosides, a novel key intermediate for coupling with different nucleobases was synthesised. Using this novel synthesis strategy comprising the novel key intermediate of the general formula III, (1S, 3R, 4R, 7S)-7-hydroxy-1-hydroxymethyl-(thymin-1-yl)-2,5-dioxabicyclo [2.2.1] heptane was synthesised in only five steps from 3-O-benzyl-4-C-hydroxymethyl-1,2-O-isopropylidene-α-D-ribofuranose, which makes the novel strategy at least two synthetic step shorter than any previously known strategy. The reduction in numbers of synthetic steps as well as the fact that no chromatographic separation of isomers and fewer deprotection steps are required makes the novel synthesis more convenient and much more cost efficient than previously known strategies. This novel synthesis strategy comprising the novel key intermediate of the general formula III also provided surprisingly facile access to [2.2.1] bicyclo nucleosides comprising other nucleobases and to intermediates which are amenable to oligomerization.

The present invention relates to a method for the synthesis of a novel intermediate with the general formula II:

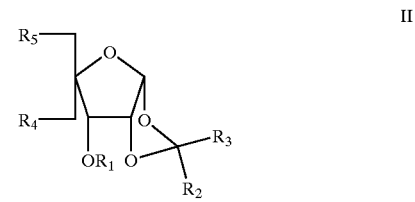

II wherein $R_1$ is selected from optionally substituted aryl($C_{1-6}$-alkyl), optionally substituted tetrahydropyran-2-yl, optionally substituted arylcarbonyl and optionally substituted aryl. Some preferred embodiments comprise benzyl, o-, m-, and p-methylbenzyl, 2-chlorobenzyl, 4-phenylbenzyl, tetrahydropyran-2-yl, benzoyl, phenyl, among which benzyl and 4-phenylbenzyl are preferred; and each of the substituents $R_2$ and $R_3$ independently is selected from hydrogen, optionally substituted $C_{1-6}$-alkyl, optionally substituted aryl, and optionally substituted aryl($C_{1-6}$-alkyl), with the proviso that $R_2$ and $R_3$ are not both hydrogen, such as methyl, trifluoromethyl, ethyl, propyl, iso-propyl, butyl, t-butyl, pentyl, cyclopentyl, hexyl, cyclohexyl, phenyl, benzyl, phenylethyl, o-, m-, and p-methylbenzyl, 2-chlorobenzyl, or $R_2$ and $R_3$ together designate $C_{3-7}$-alkylene, such as 1,3-propylene, 1,4-butylene, 1,5-pentylene; and each of the substituents $R_4$ and $R_5$ independently is R'SO$_2$—, wherein R' is selected from optionally substituted $C_{1-6}$-alkyl, optionally substituted aryl, and optionally substituted aryl($C_{1-6}$-alkyl), such as methyl, trifluoromethyl, ethyl, 2,2,2-trifluoroethyl, propyl, isopropyl, butyl, nonafluorobutyl, pentyl, cyclopentyl, hexyl, cyclohexyl, benzyl, o-, m- or p-methylbenzyl, 2-chlorobenzyl, phenyl, o-, m- or p-bromophenyl, and p-nitrophenyl.

In a preferred embodiment of the invention, the substituents $R_2$ and $R_3$ independently represent hydrogen, methyl, phenyl, benzyl, phenylethyl, preferably methyl.

In an even more preferred embodiment of the invention, the substituents $R_2$ and $R_3$ both represent methyl.

In another embodiment of the invention, each of the substituents $R_4$ and $R_5$ represent methanesulfonyl, trifluoromethanesulfonyl, ethanesulfonyl, 2,2,2-trifluoroethanesulfonyl, propanesulfonyl, iso-propanesulfonyl, butanesulfonyl, nonafluorobutanesulfonyl, pentanesulfonyl, cyclopentanesulfonyl, hexanesulfonyl, cyclohexanesulfonyl, α-toluenesulfonyl, 2-chloro-a-toluenesulfonyl, o-, m-, p-toluenesulfonyl, benzenesulfonyl, o-, m-, p-bromobenzenesulfonyl, and o-, m-, p-nitrobenzenesulfonyl, preferably methanesulfonyl, trifluoromethanesulfonyl, p-toluenesulfonyl and p-bromobenzenesulfonyl, more preferably methanesulfonyl, and p-toluenesulfonyl, even more preferably methanesulfonyl.

In a preferred embodiment of the invention, $R_4$ and $R_5$ represent methanesulfonyl, trifluoromethanesulfonyl, ethanesulfonyl, 2,2,2-trifluoroethanesulfonyl, butanesulfonyl, nonafluorobutanesulfonyl, α-toluenesulfonyl, p-toluenesulfonyl, benzenesulfonyl, p-bromobenzenesulfonyl, and p-nitrobenzenesulfonyl, preferably methanesulfonyl, trifluoromethanesulfonyl, p-toluenesulfonyl and p-bromobenzenesulfonyl, more preferably methanesulfonyl, and p-toluenesulfonyl, even more preferably methanesulfonyl.

In an especially preferred embodiment of the invention, $R_4$ and $R_5$ are identical and are selected from methanesulfonyl, trifluoromethanesulfonyl, ethanesulfonyl, 2,2,2-trifluoroethanesulfonyl, butanesulfonyl, nonafluorobutanesulfonyl, α-toluenesulfonyl, p-toluenesulfonyl, benzenesulfonyl, p-bromobenzenesulfonyl, and p-nitrobenzene-sulfonyl, preferably methanesulfonyl, trifluoromethanesulfonyl, p-toluenesulfonyl and p-bromobenzenesulfonyl, more preferably methanesulfonyl, and p-toluenesulfonyl, even more preferably methanesulfonyl.

Said method comprising the following step.

treatment of a compound with the general formula I:

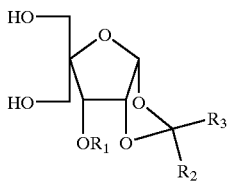

wherein $R_1$, $R_2$ and $R_3$ are as defined above;

with $R'SO_2X$ (hereinafter "sulfonyl halide(s)") wherein R' is selected from optionally substituted $C_{1-6}$-alkyl, optionally substituted aryl, and optionally substituted aryl($C_{1-6}$-alkyl), such as methyl, trifluoromethyl, ethyl, 2,2,2-trifluproethyl, propyl, iso-propyl, butyl, nonafluorobutyl, pentyl, cyclopentyl, hexyl, cyclohexyl, benzyl, o-, m- or p-methylbenzyl, 2-chlorobenzyl, phenyl, o-, m- or p-bromophenyl, p-nitrophenyl, and X designates halogen, such as fluoro, chloro, bromo, and iodo.

In a preferred embodiment of the invention, $R_1$ represent benzyl.

In another preferred embodiment of the invention, $R_2$ and $R_3$ is selected from methyl, ethyl, propyl, iso-propyl, benzyl, phenylethyl, phenyl, or $R_2$ and $R_3$ together designate 1,3-propylene, 1,4-butylene, and 1,5-pentylene.

In a more preferred embodiment of the invention, $R_2$ and $R_3$ both represent methyl.

In an especially preferred embodiment of the invention, $R_1$ represent benzyl and $R_2$ and $R_3$ both represent methyl.

In a preferred embodiment of the invention, $R'SO_2X$ represents sulfonyl halides, such as methanesulfonyl chloride, trifluoromethanesulfonyl chloride, ethanesulfonyl chloride, 2,2,2-trifluoroethanesulfonyl chloride, propanesulfonyl chloride, iso-propanesulfonyl chloride, butanesulfonyl chloride, nonafluorobutanesulfonyl chloride, cyclopentanesulfonyl chloride, hexanesulfonyl chloride, cyclohexanesulfonyl chloride, α-toluenesulfonyl chloride, p-toluenesulfonyl chloride, p-bromobenzenesulfonyl chloride, p-nitrobenzenesulfonyl chloride, preferably methanesulfonyl chloride. trifluoromethanesulfonyl chloride, ethanesulfonyl chloride, 2,2,2-trifluoroethanesulfonyl chloride, nonafluorobutanesulfonyl chloride, α-toluenesulfonyl chloride, p-toluenesulfonyl chloride, even more preferably methanesulfonyl chloride.

The ratio between compound I and sulfonyl halide is typically in the range of 1:2 to 1:10, such as 1.2–1:5, preferably 1:2–1:4, more preferably 1:2.5–1:3.5.

In one embodiment of the invention, compound I may be treated with two different sulfonyl halides, $R'''SO_2X$ and $R^{IV}SO_2X$, wherein $R'''$ and $R^{IV}$ are independently selected from the group of substituents defined for R' provided that $R'''$ and $R^{IV}$ do not represent the same group, and X is as defined above.

It should be understood that treatment of compound I with $R'''SO_2X$ and $R^{IV}SO_2X$ is performed in two separate steps. First, compound I is treated with $R'''SO_2X$ in the ratio 1:1–1:1.5, preferably 1:1–1:1.3, more preferably 1:1.1–1:1.2, to afford compound II, wherein $R_4$ or $R_5$ is $R'''SO_2O$— and $R_5$ or $R_4$ is hydroxyl. Subsequently, the formed compound II is treated with $R^{IV}SO_2X$ in the ratio 1:1–1:2.5, preferably 1:1–1:2, more preferably 1:1.1–1:1.5 to afford compound II wherein $R_4$ is $R'''SO_2O$— or $R^{IV}SO_2O$— and $R_5$ is $R^{IV}SO_2O$— if $R_4$ is $R'''SO_2O$— and $R_5$ is $R'''SO_2O$— and if $R_4$ is $R^{IV}SO_2O$—.

It should be understood that reaction of compound I with the sulfonyl halide in the presence of an anhydrous base, such as pyridine, 4-dimethylaminopyridine, imidazole, triethylamine, or sodium hydride, increase the overall yield of the reaction.

In a preferred embodiment of the invention, the treatment is performed in the presence of pyridine, imidazole, or 4-dimethylaminopyridine, preferably pyridine.

It should be clear to a person skilled in the art that other sulfonation reagents than sulfonyl halides can be used in the reaction, such as sulfonic acids and anhydrides.

For a person skilled in the art, it should also be clear that the treatment of compound I with the sulfonyl halide typically is carried out in the presence of a solvent, such as pyridine, tetrahydrofuran, toluene, xylene, benzene, ether, ethylacetate, acetonitril, triethylamine, N,N-dimethylformamide, dimethylsulfoxide, dichloromethane, and 1,2-dichloroethane.

For a person skilled in the art, it should likewise be clear that the base and the solvent may be constituted by the same substance, such as pyridine.

The treatment of compound I with sulfonyl halide is typically performed at −70° C. to 40° C., such as −30° C. to 40° C.

In a preferred embodiment of the invention, compound I is treated with sulfonyl halide at −5° C. to 30° C., preferably 0° C. to 25° C.

The present invention also relates to the compound of the general formula II as defined above.

The present invention furthermore relates to the compound of the general formula III:

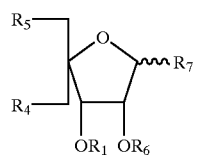

wherein $R_1$, $R_4$, and $R_5$ are as defined above; and $R_6$ is selected from hydrogen, optionally substituted ($C_{1-6}$-alkyl)carbonyl, optionally substituted arylcarbonyl, optionally substituted aryl($C_{1-6}$-alkyl), optionally substituted $C_{1-6}$-alkyl, and tri-(alkyl/aryl)silyl, such as acetyl, benzoyl, m-trifluoromethylbenzoyl, benzyl, tert-butyldimethylsilyl and tert-butyldiphenylsilyl; and $R_7$ is selected from optionally substituted ($C_{1-6}$-alkyl) carbonyloxy, optionally substituted $C_{1-6}$-alkoxy, halogen, optionally substituted arylthio, optionally substituted $C_{1-6}$-alkylthio, and optionally substituted aryloxy, such as acetyloxy, methoxy, ethoxy, chloride, fluoride, bromide or iodide, or —$SC_6H_5$.

In a preferred embodiment of the invention $R_1$ represents benzyl or 4-phenylbenzyl, most preferably 4-phenylbenzyl, and $R_4$ and $R_5$ both are selected from methanesulfonyl, trifluoromethanesulfonyl, ethanesulfonyl, 2,2,2-trifluoroethanesulfonyl, butanesulfonyl nonafluorobutanesulfonyl, α-toluenesulfonyl, p-toluenesulfonyl, benzenesulfonyl, p-bromobenzenesulfonyl, and p-nitrobenzenesulfonyl, preferably from methanesulfonyl, trifluoromethanesulfonyl, p-toluenesulfonyl and p-bromobenzenesulfonyl, more preferably methanesulfonyl, and p-toluenesulfonyl, even more preferably methanesulfonyl.

In a preferred embodiment of the invention $R_6$ is selected from acetyl, benzoyl and m-trifluoromethylbenzoyl, preferably acetyl, and $R_7$ is selected from acetyloxy, methoxy, ethoxy, chloride, flruoride, bromide, iodide and —$SC_6H_5$, preferably acetyloxy and methoxy, even more preferably acetyloxy.

In the most preferred embodiment of the invention $R_1$ represents benzyl or 4-phenylbenzyl, $R_4$ and $R_5$ both represent methanesulfonyl, $R_6$ represents acetyl, and $R_7$ represents acetyloxy.

The key intermediate with the general formula III may be coupled with suitable protected nucleobases resulting in the formation of nucleosides which undergo base-induced ring-closure to afford 2'-O, 4'-C-methylene bicyclonucleosides. It should be understood that the formed nucleosides likewise can undergo ring-closure in the presence of different amines, preferably benzylamine, and potassium thioacetate to afford the 2'-N, 4'-C-methylene- and 2'-S, 4'-C-methylene analogues, respectively.

Compounds with the general formula III may be obtained from compound II by one of the following strategies:

treatment of compound II with 80% acetic acid or trifluoroacetic acid followed by treatment of the formed intermediate with acetic anhydride (a corresponding longer chain acid anhydride) in pyridine afford compound III wherein $R_6$ is acetyl and $R_7$ is acetyloxy;

treatment of compound II with HCl in methanol (or a longer chain alcohol) afford compound III wherein $R_6$ is hydrogen and $R_7$ is methoxy (or a longer chain alkoxy). The formed compound III can be further transformed to obtain compounds of the formula III where in $R_6$ is as defined above;

treatment of compound II with HCl in methanol afford compound III wherein $R_6$ is hydrogen and $R_7$ is methoxy. Transformation of $R_6$ into one of the groups described above followed by treatment of the formed product with $HCl_{(g)}$ in dichloromethane afford compound III wherein $R_7$ is chloro and $R_6$ is as defined above;

conversion of compound II into compound III wherein $R_7$ is $C_6H_5S$— is performed as described in the literature.

Synthesis of [2.2.1]bicyclo Nucleosides

Figure 3:
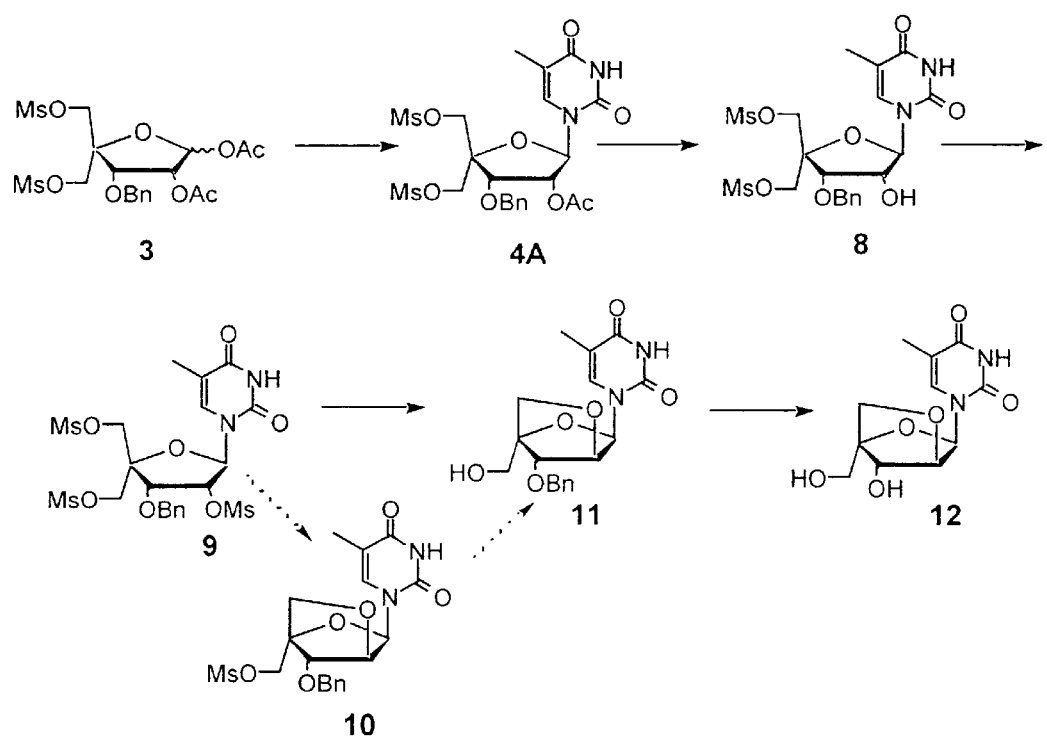
Figure 4:
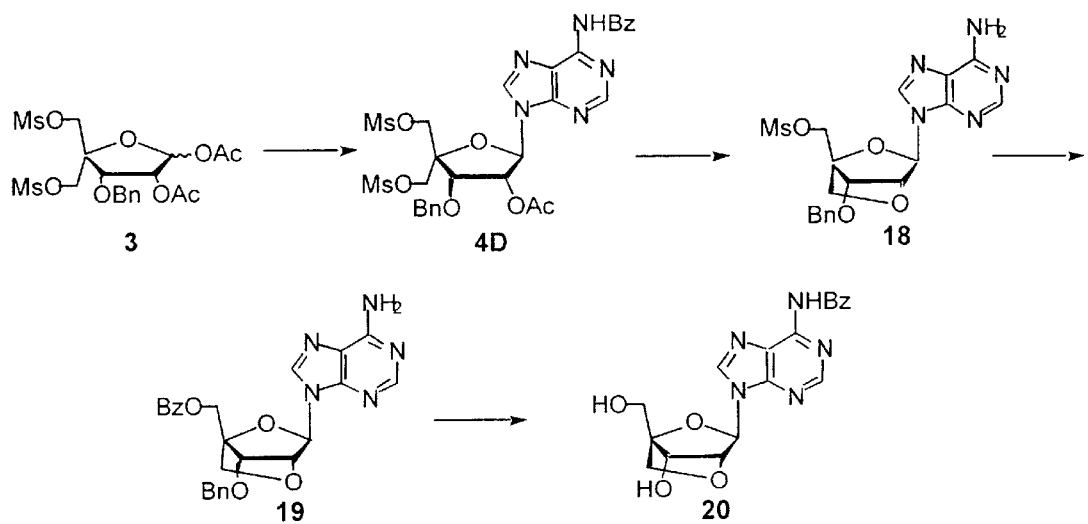
Figure 5:
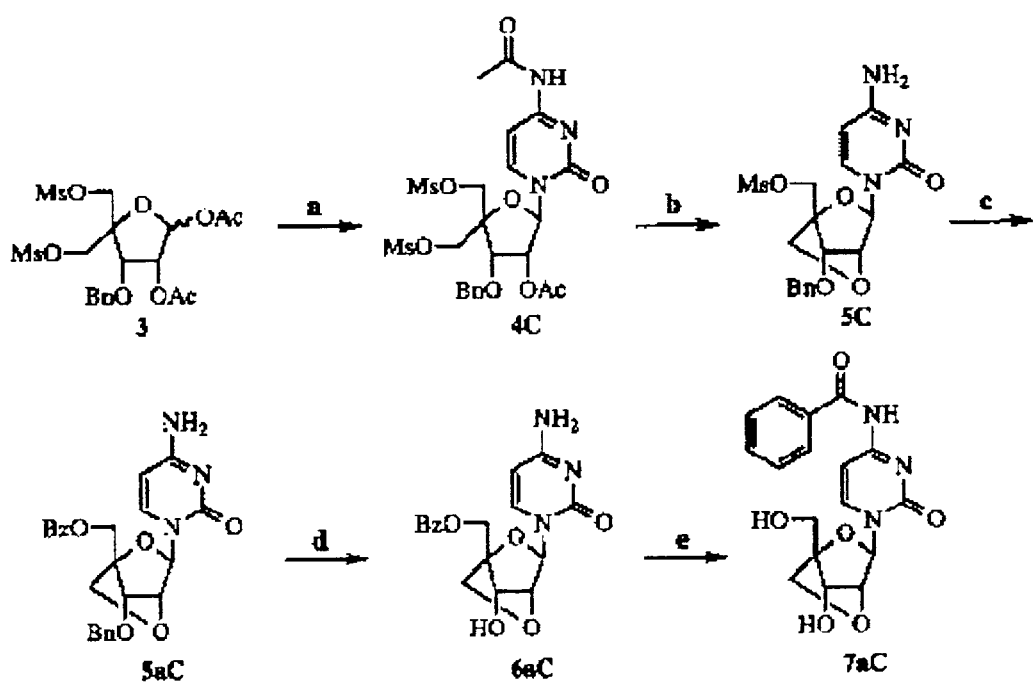

As an illustrative example of synthesis of [2.2.1]bicyclo nucleosides using the method of the present invention (1S, 3R, 4R, 7S)-7-hydroxy-1-hydroxymethyl-(thymin-1-yl)-2, 5-dioxabicyclo[2.2.1]heptane (7) was synthesized using 3-O-benzyl-4-C-hydroxymethyl-1,2-O-isopropylidene-α-D-ribofuranose (1) as starting material (FIGS. 1 and 3). Methanesulfonyl chloride (2.7 equivalents) was added to 1 (1 equivalent) in dry pyridine at 0° C. and the reaction mixture was allowed to heat to room temperature. The reaction mixture was stirred for 1 hour at room temperature affording the key intermediate 2 in 98% yield after aqueous work up. Compound 2 was used in the following step without further purification. Subsequent, acetolysis of the intermediate 2 using 80% trifluoroacetic acid followed by acetylation with acetic acid (3 equivalents) in pyridine afforded the key intermediate 3 in 92% yield. Compound 3 was coupled with silylated nucleobase using trimethylsilyl trifluoromethanesulfonate as a Lewis acid according to the methodology developed by Vorbruggen H (Vorbruggen, K., Krolikiewicz, K. and Bennua.B., *Chem. Ber.* 114, 1234–1255, (1981). Purification by silica gel flash chromatography afforded the nucleoside 4 in 85% yield. Direct based-induced ring-closure was performed by treating compound 4 with 0.5 M NaOH (1,4-dioxane:$H_2O$, 1:1) and refluxed overnight. Aqueous work-up and purification by silica gel flash chromatography afforded compound 6 in 88% yield. Catalytic hydrogenation afforded (1S, 3R, 4R, 7S)-7-hydroxy-1-hydroxymethyl-(thymin-1-yl)-2,5-dioxabicyclo[2.2.1]heptane (7) in 84% yield after crystallisation from 10% ethanol in dichloromethane.

Figure 2:
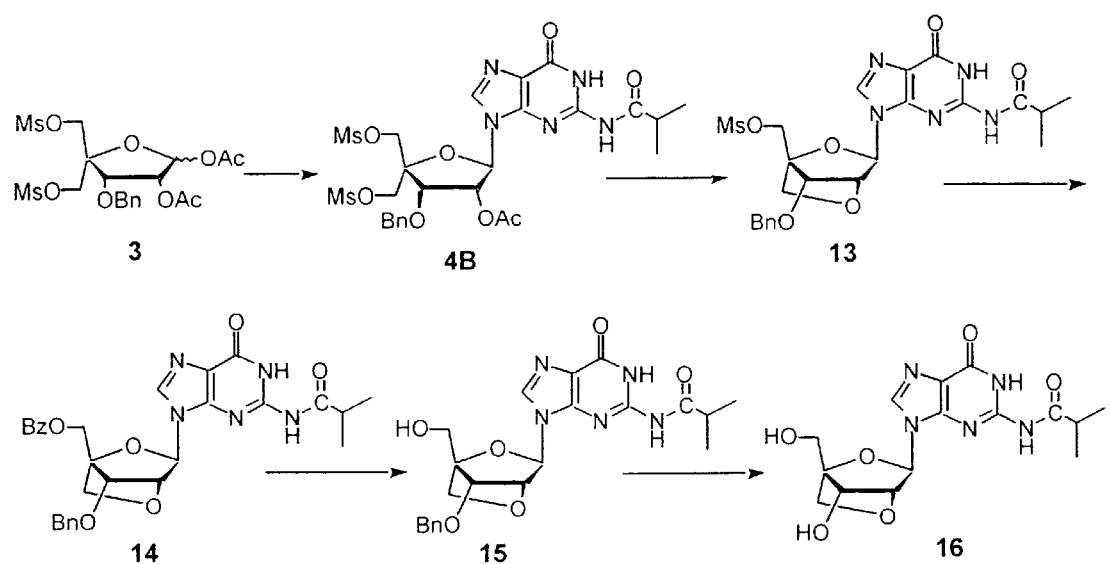

Synthesis of (1S, 3R, 4R, 7S)-7-hydroxy-1-hydroxymethyl-(guanin-9-yl)-2,5-dioxabicyclo[2.2.1] heptane was performed using the same strategy. Guanidine derivatives were also prepared by a similar strategy, such as the (1S, 3R, 4R, 7S)-7-hydroxy-1-hydroxymethyl-3-(2-N-isobutyrylguanin-9-yl)-2,5-dioxabicyclo[2.2.1]heptane 16, as illustrated by FIG. 2.

The advantageous versatility of a strategy according to this invention, wherein the key intermediate (compounds of general formula III) is employed, is further illustrated by the fact that isomers with C2' (nucleoside numbering) inversion are accessible to give α-L-ribose sugars. Thus, the thymidinyl-α-L-ribose 12 was prepared from the key intermediate. This preparation α-L-ribose [2.2.1]bicyclo nucleosides from the key intermediate has been applicable to other naturally occurring and non-naturally occurring nucleobases.

Figure 6:
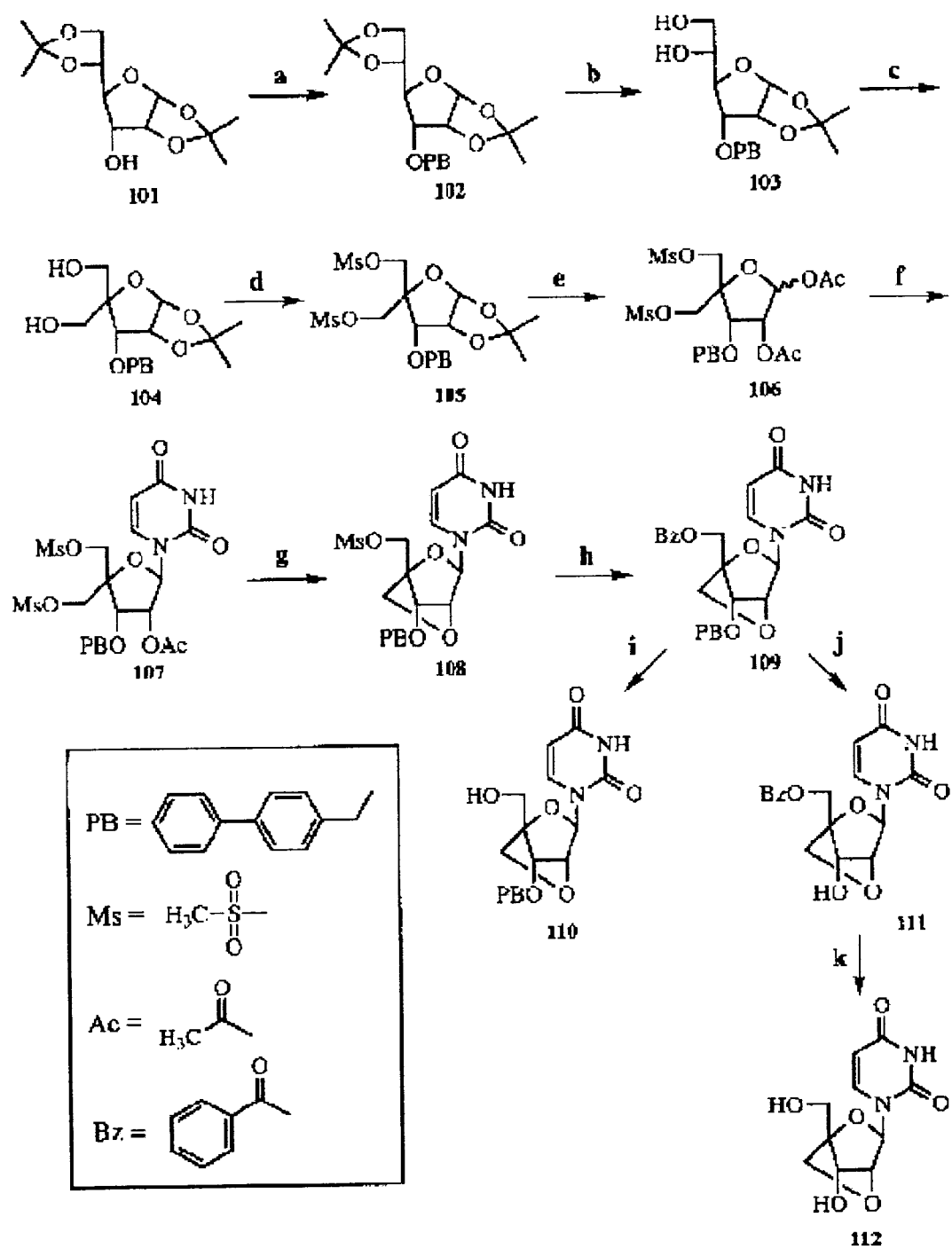
Figure 7:
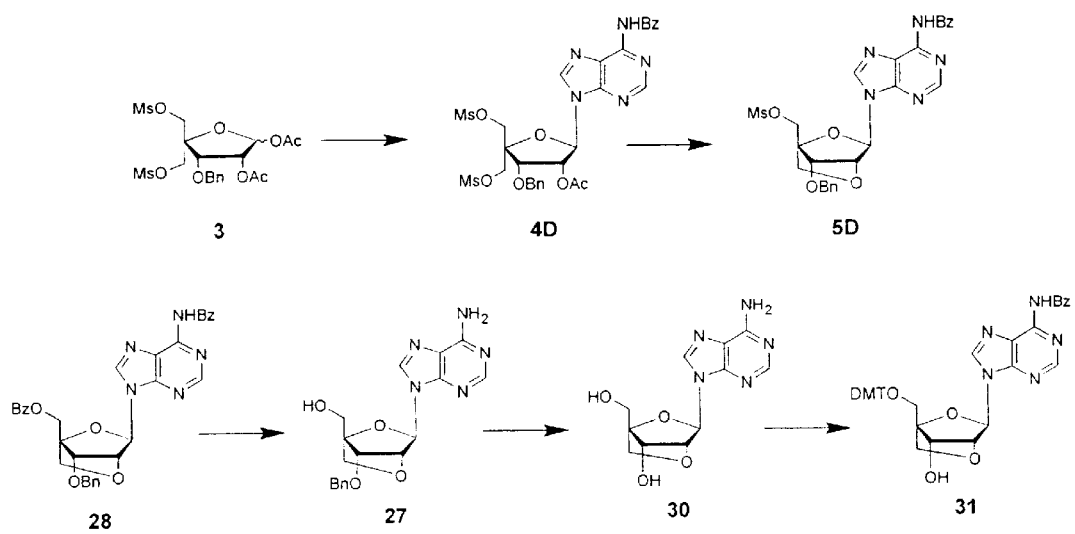
Figure 8:
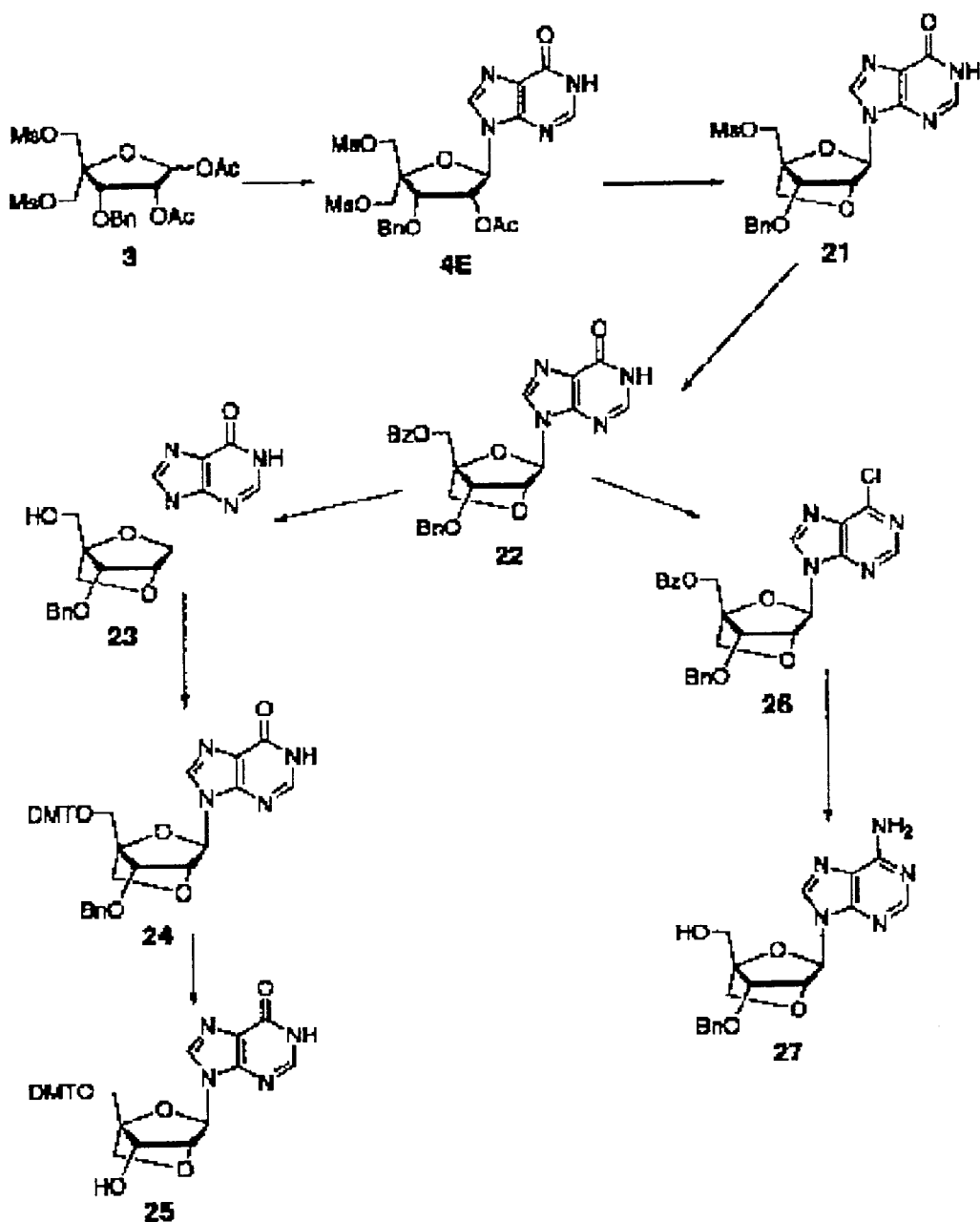

The versatility of this route is further illustrated in FIGS. 4 to 8 wherein [2.2.1]bicyclo nucleoside derivatives of adenosine, cytosine, uridine, thymidine and guanidine are accessible from the key intermediate of the general formula III. FIG. 6 illustrates a combination of preferred embodiments for compounds the general formula III for the preparation of [2.2.1]bicyclo nucleoside derivatives of uridine, wherein $R^7$ is acetoxy, $R^4$ and $R^5$ are each mesylate and $R^1$ is the aryl substituted benzyl, phenylbenzyl (labelled compound 106 in FIG. 6).

FIGURES

FIG. 1

A general synthetic route is outlines. From the known diol 1, a critical intermediate 3, may be conveniently prepared. Using the desired nucleobase or their derivatives (such as thymine, isobutyrylguanidine, N-acetylcytosine, 6-N-benzoyladenine, hypoxanthine), ribonucleoside derivatives 4A, 4B, 4C, 4D, and 4E can be accessed. Selective protective group manipulation allows for 2,4-cyclisation and access to many LNAs. This scheme is detailed in Examples 1–7.

FIG. 2

The use of key intermediate 3 to a LNA guanidine derivative 16. This scheme is detailed in Example 9.

FIG. 3

The use of key intermediate 3 to a LNA thymine derivative 12. This scheme is detailed in Example 8.

FIG. 4

The use of key intermediate 3 to a LNA adenine derivative 20. This scheme is detailed in Example 10.

FIG. 5

The use of key intermediate 3 to a LNA cytosine derivative 7aC. This scheme is detailed in Example 12.

FIG. 6

A modified route in that the bis-isoprpylidene 101 is used to access key intermediate 106, which is of the general formula III. The synthesis sequence comprises: a) $N^4$-acetylcytosine, BSA, TMSTf, $CH_3CN$; b) LiOH, THF/$H_2O$; c) Sodium benzoate, $CsCO_3$, DMF; d) $Pd(OH)_2$, cyclohexane, EtOH; e) i. Bz-Cl, pyridine, ii. NaOH, MeOH, pyridine. A different protective group strategy is used and the LNA uracil derivatives 110 and 112 are accessed. This scheme is detailed in Example 11.

FIG. 7

Different LNA adenine derivatives are accessible using key intermediate 3 These over possible advantages for later oligomerization steps. This scheme is detailed in Example 13. The synthesis sequence comprises: a) NaH, 4-chloromethylbiphenyl, THF/DMF; b) 80% AcOH; c) i. $NaIO_4$, THF/$H_2O$; ii. 37% $CH_2O$, 2M NaOH, dioxane, d) MsCl, pyridine; e) AcOH/$Ac_2O$/$H_2SO_4$; f) Uracil, BSA, TMSTf, $CH_3CN$; g) LiOH, THF/$H_2O$, h) Sodium benzoate, DMF, i) $NH_4OH$, MeOH; j) $FeCl_3$, $CH_2Cl_2$; k) $NH_4OH$, MeOH.

FIG. 8

The use of the hypoxanthine as nucleobase allows access to the LNA hypoxanthine derivative 25 and the LNA-adenine derivative 27. This scheme is detailed in Example 14.

DEFINITIONS

In the present context, the term "$C_{1-6}$-alkyl" means a linear, cyclic or branched hydrocarbon group having 1 to 6 carbon atoms, such as methyl, ethyl, propyl, iso-propyl, pentyl, cyclopentyl, hexyl, cyclohexyl, preferred examples of "$C_{1-6}$-alkyl" are methyl, ethyl, propyl, iso-propyl, butyl, tert-butyl, iso-butyl, pentyl, cyclopentyl, hexyl, cyclohexyl, in particular methyl, ethyl, propyl, iso-propyl, tert-butyl, iso-butyl and cyclohexyl.

In the present context, the term "$C_{3-7}$-alkylene" means a linear biradical having 3 to 7 carbon atoms, such as 1,3-propylene, 1,4-butylene, 1,5-pentylene, 1,6-hexylene, and 1,7-heptylene.

In the present context, i.e. in connection with the term "alkyl", the term "optionally substituted" means that the group in question may be substituted one or several times, preferably 1–3 times, with group(s) selected from hydroxyl, $C_{1-6}$-alkoxy, carboxyl, $C_{1-6}$-alkoxycarbonyl, $C_{1-6}$-alkylcarbonyl, formyl, aryl, aryloxycarbonyl, arylcarbonyl, heteroaryl, amino, mono- and di($C_{1-6}$-alkyl)amino, carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, cyano, carbamido, halogen, where aryl and heteroaryl may be substituted 1–5 times, preferably 1–3 times, with $C_{1-4}$-alkyl, $C_{1-4}$-alkoxy, nitro, cyano, amino or halogen. Especially preferred examples are hydroxyl, $C_{1-6}$-alkoxy, carboxyl, aryl, heteroaryl, amino, mono- and di($C_{1-6}$-alkyl)amino, and halogen, where aryl and heteroaryl may be substituted 1–3 times with $C_{1-4}$-alkyl, $C_{1-4}$-alkoxy, nitro, cyano, amino or halogen. Aryl and heteroaryl may be substituted as specifically describe below for "optionally substituted aryl and heteroaryl".

In the present context the term "aryl" means a fully or partially aromatic carbocyclic ring or ring system, such as phenyl, naphthyl, 1,2,3,4-tetrahydronaphthyl, anthracyl, phenanthracyl, pyrenyl, benzopyrenyl, fluorenyl and xanthenyl, among which phenyl is a preferred example.

The term "heteroaryl" means a fully or partially aromatic carbocyclic ring or ring system where one or more of the carbon atoms have been replaced with heteroatoms, e.g. nitrogen (=N— or —NH), sulphur, and/or oxygen atoms. Examples of such heteroaryl groups are oxazolyl, isoxazolyl, thiazolyl, isothiazolyl, pyrrolyl, imidazolyl, pyrazolyl, pyridinyl, pyrazinyl, pyridazinyl, piperidinyl, coumaryl, furyl, quinolyl, benzothiazolyl, benzotriazolyl, benzodiazolyl, benzooxozolyl, phthalazinyl, phthalanyl, triazolyl, tetrazolyl, isoquinolyl, acridinyl, carbazolyl, dibenzazepinyl, indolyl, benzopyrazolyl, phenoxazonyl.

In the present context, i.e. in connection with the terms "aryl" and "heteroaryl", the term "optionally substituted" means that the group in question may be substituted one or several times, preferably 1–5 times, in particular 1–3 times with group(s) selected from hydroxyl (which when present in an enol system may be represented in the tautomeric keto form), $C_{1-6}$-alkyl, $C_{1-6}$-alkoxy, oxo (which may be represented in the tautomeric enol form), carboxyl, $C_{1-6}$-alkoxycarbonyl, $C_{1-6}$-alkylcarbonyl, formyl, aryl, aryloxy, aryloxy-carbonyl, arylcarbonyl, heteroaryl, amino, mono- and di($C_{1-6}$-alkyl)amino; carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, cyano, guanidino, carbamido, $C_{1-6}$-alkanoyloxy, sulphono, $C_{1-6}$-alkylsulphonyloxy, nitro, sulphanyl, dihalogen-$C_{1-4}$-alkyl, trihalogen-$C_{1-4}$-alkyl, halogen, where aryl and heteroaryl representing substituents may be substituted 1–3 times with $C_{1-4}$-alkyl, $C_{1-4}$-alkoxy, nitro, cyano, amino or halogen. Preferred examples are hydroxyl, $C_{1-6}$-alkyl, $C_{1-6}$-alkoxy, carboxyl, $C_{1-6}$-alkoxycarbonyl, $C_{1-6}$-alkylcarbonyl, aryl, amino, mono- and di($C_{1-6}$-alkyl)amino, and halogen, wherein aryl may be substituted 1–3 times with $C_{1-4}$-alkyl, $C_{1-4}$-alkoxy, nitro, cyano, amino or halogen.

In the present context, the term "tri(alkyl/aryl)silyl" means a silyl group substituted with 0–3 alkyl groups and/or 0–3 aryl groups, with the provision that the total number of alkyl and aryl groups is 3, selected from trimethylsilyl, allyldimethylsilyl, dimethylphenylsilyl, diphenylmethylsilyl, isopropyidimethylsilyl, tert-butyldimethylsilyl, and tert-butyldiphenylsilyl, "Halogen" includes fluoro, chloro, bromo, and iodo.

In the present context, the term "nucleobase" covers naturally occurring nucleobases as well as non-naturally occurring nucleobases. It should be clear to the person skilled in the art that various nucleobases which previously have been considered "non-naturally occurring" have subsequently been found in nature. Thus, "nucleobase" includes not only the known purine and pyrimidine heterocycles, but also heterocyclic analogues and tautomers thereof. Illustrative examples of nucleobases are adenine, guanine, thymine, cytosine, uracil, purine, xanthine, diaminopurine, 8-oxo-$N^6$-methyladenine, 7-deazaxanthine, 7-deazaguanine, $N^4,N^4$-ethanocytosine, $N^6,N^6$-ethano-2,6-diaminopurine, 5-methylcytosine, 5-($C^3$-$C^6$)-alkynylcytosine, 5-fluorouracil, 5-bromouracil, pseudoiso-cytosine, 2-hydroxy-5-methyl-4-triazolopyridine, isocytosine, isoguanin, inosine and the "non-naturally occurring" nucleobases described in Benner et al., U.S. Pat. No. 5,432,272.

The term "nucleobase" is intended to cover every and all of these examples as well as analogues and tautomers thereof. Especially interesting nucleobases are adenine, guanine, thymine, cytosine, and uracil, which are considered as the naturally occurring nucleobases in relation to therapeutic and diagnostic application in humans.

In the present context, the term "nucleoside" means a glycoside of a heterocyclic base. The term "nucleoside" is used broadly as to include non-naturally occurring nucleosides, naturally occurring nucleosides as well as other nucleoside analogues. Illustrative examples of nucleosides are ribonucleosides comprising a ribose moiety as well as deoxyribonuclesides comprising a deoxyribose moiety. With respect to the bases of such nucleosides, it should be understood that this may be any of the naturally occurring bases, e.g. adenine, guanine, cytosine, thymine, and uracil, as well as any modified variants thereof or any possible unnatural bases.

EXPERIMENTAL

EXAMPLE 1

3-O-benzyl-4-C-methanesulfonoxymethyl-5-methanesulfonyl-1,2-O-isopropylidene-α-D-ribofuranose (2)

A solution of 3-O-benzyl-4-C-hydroxymethyl-1,2-O-isopropylidene-α-D-ribofuranose (1, 11.1 g, 40 mmol) (Youssefyeh, R. D.; Verheyden, J P. H.; Moffatt, J. G., *J. Org. Chem.* 1979, 44, 1301) in dry pyridine (30 mL) was cooled in an ice-bath. Methanesulfonyl chloride (8.3 mL, 108 mmol) was then added under stirring. The mixture was allowed to warm up to room temperature and stirred for 1 hr. Ether (200 mL) was added and the solution was washed with water (3×200 mL). Organic layer was dried over $Na_2SO_4$ and concentrated under reduced pressure to give 16.4 g (98%) of compound (2) as slightly yellow solid.

EXAMPLE 2

1,2-di-O-acetyl-3-O-benzyl-4-C-methanesulfonoxymethyl-5-O-methanesulfonyl-D-ribofuranose (3)

A solution of compound (2) (16 g, 34 mmol) in 80% trifluoroacetic acid (100 mL) was stirred at room temperature for 1 h. The solvents were evaporated to dryness under reduced pressure, the residue was re-dissolved in dichloromethane (200 mL) and washed by saturated aqueous $NaHCO_3$ (2×200 mL). The organic layers were dried over $Na_2SO_4$ and concentrated under reduced pressure to give colorless oily intermediate. The intermediate was co-evaporated with dry pyridine (2×50 mL), dissolved in pyridine and treated by acetic anhydride (12 mL, 103 mmol) overnight. The reaction mixture was quenched by saturated aqueous $NaHCO_3$ (250 mL) and washed by dichloromethane (2×200 mL). Organic layers were combine, dried over $Na_2SO_4$ and concentrated under reduced pressure to yield compound (3) (15.9 g, 92%) as colorless oily material.

EXAMPLE 3

1-(2-O-acetyl-3-O-benzyl-4-C-methanesulfonoxymethyl-5-O-methanesulfonyl-β-D-ribofuranosyl)thymine (4a)

N,O-bis-(trimethylsilyl)acetamide (4.4 mL, 17.8 mmol) was added to a stirred mixture of (3) (2.4 g, 4.7 mmol) and thymine (0.89 g, 7.1 mmol) in dry acetonitrile (200 mL). The reaction mixture was refluxed for 1 h before complete dissolution of thymine. Trimethylsilyl triflate (1.8 mL, 9.4 mmol) was then added dropwise and refluxing was continued for more 2 h. The reaction was cooled to room temperature, diluted with dichloromethane (200 mL) and washed by saturated aqueous solution of sodium hydrogencarbonate (2×200 mL). The organic layer was dried over $Na_2SO_4$, concentrated under reduced pressure and purified by silica gel flash chromatography using dichloromethane/methanol (98:2 v/v) as eluent to yield 2.4 g (85%) of nucleoside (4a) as a white solid material. $δ_H$ ($CD_3Cl$) 9.33 (1H, brs, NH), 7.40–7.28 (5H, m, Bn), 7.08 (1H, d, J1.2, 6-H), 5.71 (1H, d, J3.3, 1'-H), 5.58 (1H, dd, J' 6.4, J" 3.3. 2'-H), 4 70 (1H, d, J6.4, 3'-H), 4.60 (1H, d, J10.8), 4.55 (1H, d, J10.8), 4.53 (1H, d, J11.7), 4.38 (1H, d, J10.8), 4.34 (1H, d, J10.8), 4.32 (1H, d, J11.7), 3.02, 3.00 (2×3H, 2 s, methanesulfonyls), 2 11 (3H, s, acetyl), 1 92 (3H, d, J1 1, $CH_3$). $δ_C$ ($CD_3Cl$) 170.0 (C=O), 163.7 (C-6), 150.1 (C-2), 137 9, 136.6, (C-5, Bn), 128.6, 128.5, 128.4 (Bn), 111. 8 (C-4), 92.4, 840, 77 9, 74.8, 73 7, 68 4, 67 5 (ribose, Bn), 37.7, 37.6 (methanesulfonyls), 20.7 (acetyl), 12.6 ($CH_3$).

EXAMPLE 4

(1S, 3R, 4R, 7S)-7-Benzyloxy-1-methanesulfonoxymethyl-3-(thymin-1-yl)-2,5-dioxabicyclo[2.2.1]heptane (5a) and (1S, 3R, 4R, 7S)-7-Benzyloxy-1-hydroxymethyl-3-(thymin-1-yl)-2,5-dioxabicyclo[2.2.1]heptane (6a)

To a solution of compound (4a) (2 g, 3.48 mmol) in 30 mL of 1,4-dioxane were added 1 M aqueous NaOH (30 mL) and the mixture was stirred for 10 min at room temperature. TLC analysis (silica gel, 5% methanol/dichloromethane) shown quantitative conversion of starting material into a intermediate with a slightly low mobility. Analytical amount of the reaction mixture was divided by extraction in system dichloromethane/saturated aqueous $NaHCO_3$. Organic layer was washed by water, dried over $Na_2SO_4$ and concentrated under reduced pressure to give compound (5a) as a white solid material. $δ_H$ ($CD_3Cl$) 9.24 (1H, br s, NH), 7.41–7.22 (6H, m, 6-H, Bn), 5.68 (1H, s, 1'-H), 4.66 (1H, d, J, 11.5, Bn), 4.61 (1H, s, 2'-H), 4.59 (1H, d, J12.1, 5'-H), 4.56 (1H, d, J11.5, Bn), 4.52 (1H, d, J12.1, 5'-H,) 4.08 (1H, d, J7.9, 1"-H), 3.93 (1H, s, 3'-H), 3.87 (1H, d, J7.9, 1"-H), 3.08 (3H, s, methanesulfonyl), 1.93 (3H, s, $CH_3$). $δ_C$ ($CD_3Cl$) 163.6 (C-6), 149.6 (C-2), 136.3, 134.0 (C-5, Bn), 128.4, 128.2, 127.8 (Bn), 110.7 (C4), 87.5, 85.5, 76.6, 75.9, 72.3, 71.5, 64.0 (ribose, Bn), 37.8 (methanesulfonyl), 12.4 ($CH_3$).

The reaction mixture was then refluxed overnight, diluted with 200 mL of dichloromethane and washed by saturated aqueous $NaHCO_3$ (2×200 mL). Organic phase was dried, solvents were removed under reduced pressure and the residue was purified by silica gel flash chromatography using 3% methanol/dichloromethane as eluent. Compound (6a) (1.1 g, 88%) was obtained after removing of solvent as a white solid material. $δ_H$ ($CD_3Cl$) 9.28 (1H, br s, NH), 7.45 (1H, d, J1.1, 6-H), 7.38–7.22 (5H, m, Bn), 5.66 (1H, s, 1'-H), 4.67 (1H, d, J11.6, Bn), 4.56 (1H, d, J11.7, Bn), 4.54 (1H, s, 2'-H), 4.05 (1H, d, J7.9, 1"-H), 4.01 (1H, d, J12.5, 5'-H), 3.96 (1H, s, 3'-H), 3.95 (1H, d, J12.6, 5'-H), 3.83 (1H, d, J7.9, 1"-H), 1.88 (3H, d, J1.1, $CH_3$). $δ_C$ ($CD_3Cl$) 163.9 (C-6), 149.8 (C-2), 137.0, 134.7 (C-5, Bn), 128.5, 128.2, 127.8 (Bn), 110.3 (C-4), 88 2, 87.3, 76.9, 75.9, 72.3, 72.0, 57.6 (ribose, Bn), 12.7 ($CH_3$).

EXAMPLE 5

(1S, 3R, 4R, 7S)-7-Hydroxy-1-hydroxymethyl-3-(thymin-1-yl)-2,5-dioxabicyclo[2.2.1]heptane (7a)

A mixture of compound (6a) (3 g, 8.4 mmol), 20% $Pd(OH)_2$/C (1.5 g) and ammonium formate (1.6 g) was suspended in 20 mL of methanol. After refluxing the mixture for 10 min, the catalyst was filtered off through celite column and washed by methanol. All the filtrate was combined and concentrated to give a white solid material. The latter was crystallized from 10% ethanol/dichloromethane to yield 1.9 g (84%) of compound (7a) which had the same chromatographic mobility (silica TLC) and H$^1$- and C$^{13}$-NMR spectra as authentic compound (Koshkin, A. A.; Singh, S. K.; Nielsen, P.; Rajwanshi, V. K.; Kumar, R.; Meldgaard, M.; Olsen, C. E.; Wengel, *J., Tetrahedron* 1998, 54(14), 3607).

EXAMPLE 6
9-(2-O-acetyl-3-O-benzyl-4-C-methanesulfoxymethyl-5-O-methanesulfonyl-β-D-ribofuranosyl)-2-N-isobutyrylguanine (4b)

To a stirred suspension of the anomeric mixture (3) (2.3 g, 4.6 mmol) and 2-N-isobutyrylguanine (1.8 g, 7.9 mmol) in anhydrous 1,2-dichloroethane (150 mL) was added N,O-bis(trimethylsilyl)acetamide (5 mL, 20.4 mmol). The mixture was refluxed for 1 h before complete dissolution of 2-N-isobutyrylguanine. Trimethylsilyl triflate (2 mL, 11.0 mmol) was then added and the solution was stirred at reflux for more 2 h. The reaction mixture was allowed to cool to room temperature, diluted by dichloromethane (200 mL) and washed with saturated aqueous solution of sodium hydrogencarbonate (2×200 mL). The solvents were removed under reduced pressure and the residue was purified by silica gel flash chromatography in gradient concentration (1–2%) methanol/dichloromethane as eluent to give 2.1 g (68%) of white solid material consisted of three isomers (compound (4b) ca. 90% purity).

An analytical amount of (4b) was additionally purified by re-chromatography at the same conditions. $\delta_H$ (CD$_3$Cl) 12.22 (1H, brs, NHCO), 9.34 (1H, brs, NH), 7.76 (1H, s, 8-H), 7.40–7.30 (5H, m, Bn), 6.03 (1H, d, J3.9, 1'-H), 5.76 (1H, dd, J' 6.0, J" 3.9, 2"-H), 5.08 (1H, d, J6.0, 3"-H), 4.91 (1H, d, J10.5), 4.67 (1H, d, J10.9), 4.61 (2H, d, J11.1), 4.49) 1H, d, J10.5), 4.39 (1H, d, J11.0), 4.32 (1H, d, J11.7), 3.14, 3.02, (2×3H, 2 s, methansulfonyls), 2.70 (1H, m, CHCO), 2.09 (3H, s, acetyl) 1.24 (6H, m, CH$_3$CH). $\delta_C$ (CD$_3$Cl) 179.3 (COCH), 169.8 (COCH$_3$), 155.0, 148.1, 147.1 (guanine), 138.9, 136 6 (guanine, Bn), 128.6, 128.4, 128.2 (Bn), 122.2 (guanine), 88.6, 84.4, 78.2, 74.8, 74.3, 67.9, 67.4 (ribose, Bn), 37.8, 37.7, (methanesulfonyls), 36.3 (COCH), 20.6 (COCH$_3$), 19.0, 18.9 (CH$_3$CH).

EXAMPLE 7
(1S, 3R, 4R, 7S)-7-Benzyloxy-1-methanesulfonoxymethyl-3-(guanin-9-yl)-2,5-dioxabicyclo[2.2.1]heptane (5b) (1S, 3R, 4R, 7S)-7-Benzyloxy-1-hydroxymethyl-3-(guanin-9-yl)-2,5-dioxabicyclo[2.2.1]heptane (6b) and (1S, 3R, 4R, 7S)-7-Hydroxy-1-hydroxymethyl-3-(guanin-9-yl)-2,5-dioxabicyclo[2.2.1]heptane (7a)

Nucleoside (4b) was dissolved in 0.5 M aqueous sodium hydroxide and kept at ambient temperature. The reaction was followed by RP-HPLC analysis in system A:

Column: Delta-Pack, C18, 100 Å, 3.9×150 mm.

Gradient: 0 to 50% acetonitrile in water (0.05 M triethylammonium acetate, pH 7.0) during 15 min.

Flow rate: 1.5 mL/min.

Starting material (4b) (retention time 19.5 min) was fully consumed during 1 h at ambient temperature to give a number of intermediate products. The main product had retention time of 17.9 min and was assumed to be the 2-N-isobutyryl protected derivative of nucleoside 5b. The complete removal of isobutyryl group was observed after 12 h of reaction (5b: retention time 14.7 min; ca.90% purity by HPLC analysis). Only trace amounts of nucleoside (6b) have been found in the reaction mixture. The reaction proceed at reflux for more 12 h which resulted in full conversion of (5b) to (6b) (retention time 12.6 min). The reaction mixture was neutralized by acetic acid (to pH 7), filtered through silica gel column and concentrated under reduced pressure. Analytical amount of compound (6b) was purified by semi-prep RP-HPLC (Nucleosil C18, 10×30 mm) using the same solvents as in system A. Compound (6b) (ca. 10 mg) was dissolved in methanol, 10% Pd/C (50 mg) and ammonium format (20 mg) were added and the mixture was refluxed for 15 min. Analysis of the reaction mixture in system A shown a quantitative formation of compound (7b) (retention time 4.7 min) with the same mobility as authentic compound prepared by method described earlier (Koshkin, A. A.; Singh, S. K.; Nielsen, P.; Rajwanshi, V. K.; Kumar, R.; Meldgaard, M ; Olsen, C. E.; Wengel, *J., Tetrahedron* 1998, 54(14), 3607).

EXAMPLE 8
1-(3-O-benzyl-4-C-methanesulfonoxymethyl-5-O-methanesulfonyl-β-D-ribofuranosyl)thymine (8)

To a solution of compound 4a (2.8 g, 4.8 mmol) in 1,4-dioxane (10 mL) was added concentrated ammonium hydroxide solution (30%, 1 mL). After 4 h, the solvents were removed under reduced pressure, the residue re-dissolved in dichloromethane and applied for silica gel HPLC using 0 to 3% methanol/dichloromethane mixture as eluent to yield 2.05 g (78%) of compound 8 as a white solid material.

1-(3-O-benzyl-4-C-methanesulfonoxymethyl-2,5-di-O-metha nesulfonyl-β-D-ribofuranosyl)thymine (9)

Compound 8 (2 g, 3.7 mmol) was co-evaporated with anhydrous pyridine (2×50 mL), dissolved in pyridine (50 mL) and reacted with methanesulfonyl chloride (0.35 mL, 4.5 mmol) overnight. The mixture was diluted with dichloromethane (100 mL), washed with saturated aqueous NaHCO$_3$ (2×100 mL) and concentrated under reduced pressure Column silica gel chromatography (2% methanol/dichloromethane as eluent) yielded compound 9 (2.1 g, 92%) as white solid material. $\delta_H$ (CDCl$_3$) 9.67 (1H, s, NH), 7.38–7.15 (6H, m, 6-H, Bn), 5.81 (1H, d, J 2.4, 1'-H), 5.58 (1H, dd, J' 6.5, J" 2.4, 2'-H), 4.75 (1H, d, J 11.0), 4.73 (1H, d, J 6.6, 3'-H), 4.60 (1H, d, J 10.8), 4.53 (1H, d, J 11.5), 4.41 (1H, d, J 11.0), 4.35 (1H, d, J 11.0), 4.33 (1H, d, J 11.6), 3 20, 3 12, 3.00 (3×3H, 3 s, methanesulfonyls), 1.91 (3H, d, J 1.1, 5-CH$_3$). $\delta_C$ (CDCl$_3$) 163.7 (C-6), 150.3 (C-2), 137.8, 136.2 (C-5, Bn), 128.6, 128.5, 128.4, 128.3 (Bn), 111.7 (C-4), 93.1, 84.2, 77.6, 76.8, 74.1, 68.1, 67.5, (ribose, Bn), 38.5, 37.5, 37.4 (methanesulfonyls), 12.1 (5-CH$_3$).

(1R, 3R, 4S, 7S)-7-Benzyloxy-1-methanesulfonoxymethyl-3-(thymin-1-yl)-2,5-dioxabicyclo[2.2.1]heptane (10)

Compound 9 (105 mg, 0.17 mmol) was dissolved in a mixture of dioxane and water (2:1, 15 mL). 2 M aqueous solution of NaOH was added by portions of 100 uL every 0.5 hrs and the reaction was followed by analytical TLC (silica gel, 5% methanol/dichloromethane). Two intermediates with lower mobility were detected in the reaction mixture which were completely converted to a single product after addition of 1 mL of aqueous NaOH solution. The product was extracted by dichloromethane (50 mL), washed with saturated aqueous NaHCO$_3$ (50 mL) and brine (40 mL), and dried over Na$_2$SO$_4$. Concentration under reduced pressure gave 72 mg (96%) of compound 10 as a white solid material. $\delta_H$ (CDCl$_3$) 8.90 (1H, br s, NH), 7.48–7.34 (6H, m, 6-H, Bn), 6.27 (1H, s, 1'-H), 4.72 (1H, d, J 11.7), 4.66 (1H, d, J 11.7), 4.56 (1H, d, J 11.7), 4.48 (1H, d, J 11.7), 4.48 (1H, dd, J' 2.4, J" 1.1, 2'-H), 4.25 (1H, d, J 2.4, 3'-H), 4.10 (1H, d, J 9.1), 4.05 (1H, d, J 9.0), 3.05, (3H, s, methanesulfonyl), 1.95 (3H, d, J 1.1, 5-CH$_3$). $\delta_C$ (CDCl$_3$) 163.5 (C-6), 150.1 (C-2), 136.2, 135.5 (C-5, Bn), 128.7, 128.6, 128.1, (Bn), 109.9

(C-4), 90.0, 86.0, 81.7, 75.9, 73.2, 67.0, 65.1 (ribose, Bn), 37.5, (methanesulfonyl), 12.6 (5-CH$_3$).

(1R, 3R, 4S, 7S)-7-Benzyloxy-1-hydroxymethyl-3-(thymin-1-yl)-2,5-dioxabicyclo[2.2.1]heptane (11)

Compound 9 (1.8 g, 2.94 mmol) was suspended in 0.5 M solution of aqueous NaOH (1,4-dioxane/water 1/1, 80 mL) and the mixture was heated at 90° C. for 48 hrs. The solution was cooled to room temperature, diluted with dichloromethane (100 mL) and washed with saturated aqueous NaHCO$_3$ (2×100 mL). The organic layer was dried over Na$_2$SO$_4$ and concentrated in vacuo. The final product (compound 11, 800 mg, 76%) was purified by silica gel column chromatography using 1 to 4% solution of ethanol/dichloromethane as eluent. $\delta_H$ (CDCl$_3$) 9.38 (1H, br s, NH), 7.52 (1H, d, J 1.1, 6-H), 7.40–731 (5H, m, BN), 6.24 (1H, s, 1'-H), 4.72 (1H, d, J 11.9), 4.65 (1H, d, J 11.9), 4.48 (1H, dd, J' 2.2, J" 0.8, 2'-H), 4.22 (1H, d, J 2.3, 3'-H), 4.08 (1H, d, J 9.7), 4.05 (1H, d, J 12.3), 4.02 (1H, d, J 9.8), 3.91 (1H, d, J 12.2), 1.92 (3H, d, J 1.1, 5-CH$_3$). $\delta_C$ (CDCl$_3$) 164.0 (C-6), 150.3 (C-2), 136.6, 135.9 (C-5, Bn), 128.6, 128.3, 127.8 (Bn), 109.5 (C-4), 89.8, 88.5, 81.8, 76.0, 73.8, 72.9, 59.0 (ribose, Bn), 12.5 (5-CH$_3$).

(1R, 3R, 4S, 7S)-7-Hydroxy-1-hydroxymethyl-3-(thymin-1-yl)-2,5-dioxabicyclo[2.2.1]heptane (12)

A mixture of compound 11 (750 mg, 2.09 mmol) and 10% Pd/C (500 mg) was suspended in methanol (20 mL) and sodium formate (700 mg, 11.1 mmol) was added. The reaction was conducted at refluxing for 10 min and cooled to ambient temperature. The catalyst was filtered off and the mixture was concentrated under reduced pressure to give compound 12 (540 mg, 96%) as a white solid material.

$\delta_H$ (DMSO-d$_6$) 11.32 (1H, br s, NH), 7.64 (1H, s, 6-H), 6.09 (1H, s, 1'-H), 5.91 (1H, d, J 3.1, 3'-OH), 4.94 (1H, br s, 5'-OH), 4.31, 4,17 (2×s, 2'-H, 3'-H), 4.03 (2H, s, 1"-H), 3.71 (2H, s, 5'-H), 1.82 (3H, s, 5-CH$_3$). $\delta_C$ (DMSO-d$_6$) 163.9 (C-6), 150.4 (C-2), 136.5 (C-5), 108.0 (C-4), 89.2, 89.1, 77.3, 74.7, 73.6, 57.2 (ribose), 12.3 (5-CH$_3$).

EXAMPLE 9

(1S, 3R, 4R, 7S)-7-Benzyloxy-1-methanesulfonoxymethyl-3-(2-N-isobutyrylguanin-9-yl)-2,5-dioxabicyclo[2.2.1]heptane (13)

Compound 4b (1 g, 1.49 mmol) was dissolved in an aqueous 0.5 M NaOH/dioxane mixture (1:1, 20 mL) and the solution was kept at room temperature for 15 min. Dichloromethane (20 mL) was added and the mixture was washed with saturated NaHCO$_3$ (2×30 mL). After separation organic layer was dried over Na$_2$SO$_4$, concentrated under reduced pressure, and the residue was purified by column silica gel chromatography using 0 to 4% methanol/dichloromethane as eluent to yield 620 mg (78%) of compound 13 as a white solid material.

$\delta_H$ (CDCl$_3$) 12.14 (1H, br s, NHCO), 9.51 (1H, br s, NH), 7.77 (1H, s, 8-H), 7.30–7.26 (5H, m, Bn), 5.84 (1H, s, 1'-H), 4.67 (1H, d, J 11.5), 4.63 (1H, d, J 12.0), 462 (1H, s, 2'-H), 4.62 (1H, d, J 11.5), 4.56 (1H, d, J 11.9), 4.50 (1H, s, 3'-H), 4.12 (1H, d, J 8.0, 1"-H), 3.93 (1H, d, J 7.9, 1"-H), 3.06 (3H, s, methanesulfonyl), 2.77 (1H, m, CHCO), 1.26 (6H, m, CH$_3$).

(1S, 3R, 4R, 7S)-7-Benzyloxy-1-benzoyloxymethyl-3-(2-N-isobutyrylguanin-9-yl)-2,5-dioxabicyclo[2.2.1]heptane (14)

A mixture of compound 13 (600 mg, 1.26 mmol) and sodium benzoate (310 mg, 2.16 mmol) was suspended in anhydrous DMF (25 mL) and heated at 100° C. for 4 h under intensive stirring. The solution was cooled to ambient temperature, diluted with dichloromethane (50 mL) and filtered through glass filter. The filtrate was washed with saturated aqueous solution of NaHCO$_3$ (2×50 mL), dried over Na$_2$SO$_4$ and concentrated under reduced pressure. The final product was purified by silica gel column chromatography (1 to 2.5% methanol/dichloromethane as eluent) to yield 560 mg (89%) of compound 14 as a white solid material. $\delta_H$ (CDCl$_3$) 12.12 (1H, br s, NHCO), 9.30 (1H, br s, NH), 7.92 (m, 2H, Bz), 7.72 (1H, s, 8-H), 7.57 (1H, m, Bz), 7.42 (2H, m, Bz), 7 24-7.20 (5H, m, Bn), 5.81 (1H, s, 1'-H), 4.80 (1H, d, J 12.6), 4.66 (1H, s, 2'-H), 4.64 (1H, d, J 12.0), 4.61 (1H, d, J 12.7), 4.21 (1H, d, J 8.1, 1"-H), 4.20 (1H, s, 3'-H), 4.00 (1H, d, J 7.9, 1"-H), 2.77 (1H, m, CHCO), 1.27 (6H, m, CH$_3$). $\delta_C$ (CDCl$_3$) 178.8 (CHCO), 165.7 (Bz), 154.9, 147.8, 146.9 (guanine), 136.4, 135.3, 133.4 (guanine, Bn, Bz), 129.3, 129.0, 128.6, 128.5, 128.2, 128.7 (Bn, Bz), 121.0 (guanine), 86.2, 85.5, 77.1, 72.4, 72.1, 59.3 (ribose, Bn), 36.2 (CHCO), 18.8 (CH$_3$CH).

(1S, 3R, 4R, 7S)-7-Benzyloxy-1-hydroxymethyl-3-(2-N-isobutyrylguanin-9-yl)-2,5-dioxabicyclo[2.2.1]heptane (15)

To a solution of compound 14 (8.2 g, 14.7 mmol) in ethanol/pyridine (8:1, 450 mL) was added 2 M aqueous solution of NaOH (15.5 mL) and the mixture was stirred for 30 min at ambient temperature. Acetic acid (25 mL) was added to the reaction mixture and the solvents were removed under reduced pressure. The residue was crystallised from 20% aqueous ethanol to give 5.8 g (87%) of compound 15 as a white solid material. $\delta_H$ (DMSO-d$_6$) 8.05 (1H, s, 8-H), 7.33–7.26 (5H, m, Bn), 5.85 (1H, s, 1'-H), 5.17 (1H, t, J 5.4, 5'-OH), 4.69 (1H, s, 2'-H), 4.64 (2H, s, Bn), 4.23 (1H, s, 3'-H), 3.95 (1H, d, J 7.9, 1"-H), 3.83 (2H, m, 5'-H), 3.80 (1H, d, J8.0, 1"-H), 2.78 (1H, m, CHCO), 1.12 (6H, m, CH$_3$). $\delta_C$ (CDCl$_3$) 180.2 (CHCO), 154.8, 148.2, 147.7 (guanine), 137.9, 136.3, (guanine, Bn), 128.3, 127.6, 127.5 (Bn), 120.5 (guanine), 88.2, 85.2, 76.9, 72.1, 71.3, 56.7 (ribose, Bn), 34.8 (CHCO), 18.9 (CH$_3$CH).

(1S, 3R, 4R, 7S)-7-Hydroxy-1-hydroxymethyl-3-(2-N-isobutyrylguanin-9-yl)-2,5-dioxabicyclo[2.2.1]heptane (16)

To a solution of compound 15 (5.8 g, 12.7 mmol) in methanol (50 mL) was added 10% Pd/C (2 g) and formic acid (3 mL). The mixture was refluxed for 5 h, cooled to ambient temperature and filtrated through silica gel column. The column was washed with methanol (50 mL), all the filtrate was concentrated under reduced pressure to yield 4.55 g (98%) of compound 16 as a glass-like solid.

EXAMPLE 10

1-(2-O-acetyl-3-O-benzyl-4-C-methanesulfonoxymethyl-5-O-methanesulfonyl-β-D-ribofuranosyl)-6-N-benzoyladenine (4D)

To a suspension of compound 3 (4.8 g, 9.4 mmol) and 6-N-benzoyladenine (2.7 g, 11.3 mmol) in anhydrous 1,2-dichloroethane (40 mL) was added BSA (5.9 mL, 23.8 mmol) and the mixture was refluxed for 1 h. Then trimethylsilyl triflate (2.6 mL, 14.3 mmol) was added, the reaction was refluxed for more 4 h and kept at room temperature overnight. The reaction mixture was diluted with dichloromethane (100 mL), washed with saturated aqueous NaHCO$_3$ (200 mL), concentrated under reduced pressure, and the product was purified by column silica gel chromatography (1 to 3% of methanol/dichloromethane as eluent). Yield 3.5 g (53%) of compound 17 as yellow foam. $\delta_H$ (CD$_3$Cl) 8.76 (1H, s, 8-H), 8.12 (1H, s, 2-H), 8.02 (2H, m, Bz), 7.61 (1H, m, Bz), 7.51 (2H, m, Bz), 7.40–7.34 (5H, m, Bn), 6.23 (1H, d, J3.5, 1'-H), 6.08 (1H, dd, J' 5.9, J" 3.5, 2'-H), 5.12 (1H, d, J 6.0, 3'-H), 4.68 (1H, d, J 11.1), 4.67 (1H, d, J 11.6), 4.64 (1H, d, J 11.0), 4.44 (1H, d J 10.8), 4.39 (1H, d, J 11.7), 4.36 (1H, d, J 11.0), 3.03, 2.87 (2×3H, 2 s, methanesulfonyls), 2.13 (3H, s, acetyl). $\delta_C$ (CD$_3$Cl) 169.5 (CH$_3$CO), 164.5 (Bz), 152.5, 150.9, 149.7, 142.4 (adeninyl), 136.3, 133.2, 132.8, 128.7, 128.5, 128.4, 128.3, 128.2, 128.0, 127.9, 127.8 (Bn, Bz), 123.5 (adeninyl), 87.8, 84.1, 77.3, 74.6, 73.4, 67.3, 67.2 (ribose, Bn), 37.6, 37.3 (methanesulfonyls), 20.5 (acetyl).

(1S, 3R, 4R, 7S)-7-Benzyloxy-1-methanesulfonoxymethyl-3-(adenin-9-yl)-2,5-dioxabicyclo-[2.2.1]heptane (18)

To a solution of compound 17 (2.5 g, 3.6 mmol) in 1,4-dioxane (20 mL) was added concentrated ammonium hydroxide (30%, 20 mL). The solution was kept at room temperature overnight and diluted with aqueous NaOH (2 M, 5 mL). 30 Min later the solvents were removed under reduced pressure and the residue was suspended in dichloromethane (100 mL), washed with saturated $NaHCO_3$ (100 mL), dried over $Na_2SO_4$, and concentrated to a solid foam. Finally, the product was purified by column silica gel chromatography using 2 to 5% of methanol in dichloromethane as eluent to yield 1.26 g (78%) of compound 18 as a yellow solid material. $\delta_H$ ($CD_3Cl$) 8.30 (1H, s, 8-H), 7.90 (1H, s, 2-H), 7.31–7.27 (5H, m, Bn), 6.04 (1H, s, 1'-H), 4.93 (1H, s, 2'-H), 4.68 (1H, d, J 11.7), 4.60 (1H, d, J 11.7), 4.59 (1H, d, J 11.7), 4.57 (1H, d, J 11.9), 4.35 (1H, s, 3-H), 4.19 (1H, d, J 7.9, 1"-H), 4.02 (1H, d, J7.9, 1"-H), 3.03 (3H, s, methanesulfonyl). $\delta_C$ ($CD_3Cl$) 155.4 (C-6), 152.9 (C-2), 148.6 (C-4), 138.0 (C-8), 136.4, 128.4, 128.2, 127.8 (Bn), 119.7 (C-5), 86.6, 85.1, 77.5, 76.8, 72.4, 72.2, 64.4 (ribose, Bn), 37.7 (methanesulfonyl).

(1S, 3R, 4R, 7S)-7-Benzyloxy-1-benzoyloxymethyl-3-(adenin-9-yl)-2,5-dioxabicyclo-[2.2.1]heptane (19)

Sodium benzoate (0.77 g, 5.38 mmol) was added to a solution of compound 18 (1.2 g, 2.69 mmol) in anhydrous DMF (50 mL). The mixture was stirred at 80° C. overnight, cooled to room temperature and filtered through a glass filter. The filtrate was diluted with dichloromethane (100 mL), washed with saturated aqueous $NaHCO_3$, dried over $Na_2SO_4$, and concentrated under reduced pressure. The desired compound was purified by silica gel chromatography (1.5 to 4% methanol in dichloromethane) and crystallised from ethanol to yield 1.04 g (82%) of compound 19 as a white solid material. $\delta_H$ (DMSO/methanol 1/10) 8.16 (1H, s, 8-H), 8.03 (1H, s, 2-H), 8.02 (2H, m, Bz), 7.63 (1H, m, Bz), 7.47 (2H, m, Bz), 7.29–7.18 (5H, m, Bn), 6.07 (1H, s, 1'-H), 4.87 (1H, s, 2'-H), 4.83 (1H, d, J 12.8), 4.71 (1H, d, J 11.9), 4.70 (1H, d, J12.8), 4.62 (1H, d, J 11.9), 4.47 (1H, s, 3'-H), 4.23 (1H, d, J 8.0, 1"-H), 4.05 (1H, d, J 7.9, 1"-H).

(1S, 3R, 4R, 7S)-7-Hydroxy-1-hydroxymethyl-3-(6-N-benzoyladenin-9-yl)-2,5-dioxabicyclo-[2.2.1]heptane (20)

A mixture of compound 19 (0.95 g, 2.01 mmol) and $Pd(OH)_2$/C (20%, 1 g) was suspended in methanol/cyclohexene (1:1, 20 mL) and refluxed overnight. The reaction mixture was cooled to rt, filtered through Celite™ column, and concentrated under reduced pressure. The residue was co-evaporated with anhydrous pyridine (2×20 mL), dissolved in anhydrous pyridine, and cooled in ice-bath. Benzoyl chloride (1.15 mL, 10 mmol) was added dropwise and the mixture was stirred at RT for 20 h. Reaction was then quenched by addition of ice-cold water (40 mL), and washed with dichloromethane (2×50 mL). The organic layers were combined, concentrated under reduced pressure, re-dissolved in pyridine/methanol (1:2, 30 mL), and 2 M aqueous NaOH (5 mL) was added. After 15 min, the mixture was neutralised with acetic acid (5 mL) and solvents were removed to give an oily residue. The latter was suspended in 5% methanol/dichloromethane, applied to a silica gel column and eluted by 5 to 15% of methanol/dichloromethane as a solvent. The fractions containing compound 20 were concentrated to yield 0.54 g (70%) of glass-like solid material with the same chromatographic mobility as authentic compound.

EXAMPLE 11

Preparation of Diol 104

Sodium hydride (1.15 g of a 60% dispersion in mineral oil, 28.75 mmol) was suspended in dry DMF (10 mL) under $N_2$ and cooled in an ice bath. A mixture of 1,2:5,6-di-O-isopropylidene-α-D-allofuranose 101 (5.0 g19.21 mmol) and 4-(chloromethyl)-biphenyl (4.67 g, 23.04 mmol, Fluka, >97%) in dry THF (50 mL) was added dropwise over 45 min. The cooling bath was removed and the mixture was stirred at room temperature for 24 h. The brownish mixture was cooled in an ice bath and water (20 mL) was carefully added. Layers were separated and the aqueous layer was extracted with ether (50 mL). The combined organic layers were washed with water (2×50 mL) and brine (50 mL), dried ($Na_2SO_4$) and evaporated under reduced pressure. To the resulting brown oil, which crystallised on standing, was added 80% acetic acid (40 mL) and the reaction mixture was stirred at room temperature for 24 hours. The mixture was extracted with light petroleum ether (2×25 mL) and the acetic acid was evaporated under reduced pressure followed by co-evaporation with ethanol. The residue was partitioned between $CH_2Cl_2$ (100 mL) and saturated aqueous $NaHCO_3$ (50 mL). Layers were separated and the aqueous layer was extracted with $CH_2Cl_2$ (100 mL). The combined organic layers were washed with brine (50 mL), dried ($Na_2SO_4$) and evaporated under reduced, affording a sticky pale yellow foam (6.9 g). This crude 5,6-diol product 103 (6.9 g) was dissolved in THF/$H_2O$ (50% v/v, 100 mL) and $NaIO_4$ (4.6 g, 21.51 mmol) was added. The reaction mixture was stirred at room temperature for 60 min. and the resulting thick white slurry was filtrated. The formed precipitate was washed with ether (100 mL) and the combined filtrates were extracted with ether (2×100 mL). The combined organic layers were washed with water (2×100 mL) and brine (100 mL). The solvents were removed under reduced pressure and p-dioxane (40 mL) was added to this crude aldehyde product. To the stirred solution was added 37% aqueous formaldehyde (4.0 mL) followed by addition of 2 M aqueous NaOH (18 mL) and the reaction mixture was stirred at room temperature for 21 hours. Saturated aqueous $NaHCO_3$ (100 mL) was added and the mixture was extracted with $CH_2Cl_2$ (3×200 mL). The combined organic layers were washed with saturated aqueous $NaHCO_3$ (100 mL), dried ($Na_2SO_4$) and evaporated under reduced pressure. The residual pale yellow solid material was recrystallised from ether and gave diol 104 as a white solid material (3.7 g). The remaining material in the mother liqueur was not further purified for the time being. $^1H$ NMR (400 MHz, $CDCl_3$) δ: 1.34 (3H, s, $CH_3$), 1.65 (3H, s, $CH_3$) 3.61 (1H, "d", J 12.08, H-1"a) 3.81 (1H, d, J 12.10, H-1"b), 3.91 (1H, d, J 10.78, H-5'a) 3.96 (1H, d, J 10.78, H-5'b), 4.26 (1H, d, J 5.31, H-3'), 4.61(1H, d, J 11.72, phenylbenzyl-CHa), 4.68 (1H, dd, J 4.03 and 5.13, H-2'), 4.84 (1H, d, J 11.72, phenylbenzyl-CHb), 5.78 (1H, d, J 3.84, H-1'), 7.36–7.58 (5H, m, Ar), 7.59-60 (4H, m, Ar). $^{13}C$ NMR (400 MHz, $CDCl_3$) δ: 25.78, 26.45 (C($CH_3$)$_2$, isopylidene), 63.13, 64.14, 72.30, 77.22, 78.31 (C-1", C-5', $CH_2$-phenylbenzyl, C-3', C-2'), 86.16 (C-4'), 104.32 (C-1'), 113.40 ($C(CH_3)_2$), 126.96, 127.17, 127.29, 128.14, 128.66, 136.08, 140.53, 141.00 (Ar).

Preparation of bis-mesylate 105

To a stirred solution of diol 104 (3.69 g, 9.55 mmol) in dry pyridine (25 mL) under $N_2$ at 0–5° C. was added methanesulfonyl chloride (1.86 mL, 24.03 mmol) dropwise. The cooling bath was removed and the reaction mixture was stirred at room temperature for 2.5 hours. The mixture was diluted with ether (100 mL) and washed with saturated aqueous $NaHCO_3$ (2×30 mL), 1 M NaOH (2×30 mL), water (30 mL) and brine (30 mL). The organic solution was dried (MgSO$_4$) and the solvents were evaporated under reduced pressure. Residual pyridine was removed by co-evaporation with toluene and drying under high vacuum over night. The crude bis-mesylate product 5 (4.75 g, 92% yield, yellow foam) was used without further purification.

Preparation of bis-acetyl 106

Crude bis-mesylate 105 (4.75 g, 8.75 mmol) was dissolved in a mixture of acetic acid (70 mL) and acetic anhydride (7.0 mL) under N$_2$. To the stirred mixture was added concentrated H$_2$SO$_4$ (0.07 mL) and the resulting reaction mixture was stirred at room temperature for 3 hours. The mixture was poured into water (150 mL) containing some ice and stirred for 20 min. Then saturated aqueous NaHCO$_3$ (100 mL) and CH$_2$Cl$_2$ (200 mL) was added and the mixture stirred for 30 min. Layers were separated and the organic layer was washed with saturated aqueous NaHCO$_3$ (2×100 mL), dried (Na$_2$SO$_4$) and evaporated under reduced pressure. The remaining brown oil was purified by column chromatography on silica: packed in CH$_2$Cl$_2$; elution with 0–2% MeOH in CH$_2$Cl$_2$, v/v and gave bis-acetylated compound 106 (3.91 g, 76% yield) as a white foam.

Preparation of Nucleoside 107

Anomeric mixture 106 (3.91 g, 6.65 mmol) was dissolved in dry CH$_3$CN (40 mL) under N$_2$. Uracil (894 mg, 7.98 mmol) was added followed by dropwise addition of N,O-bis(trimethylsiiyl)acetamide (8.3 mL, 33.58 mmol). The slightly turbid solution was heated to 40° C. and stirred at this temperature for 40 min. The clear yellow solution was cooled to room temperature and trimethylsilyl triflate (1.54 mL, 7.97 mmol) was added dropwise. The reaction mixture was heated to reflux and stirred at this temperature for 5 hours. The mixture was cooled to room temperature and stirred over night. The mixture was diluted with CH$_2$Cl$_2$ (150 mL) and washed with saturated aqueous NaHCO$_3$ (3×50 mL), dried (Na$_2$SO$_4$) and evaporated under reduced pressure. The residue was subjected to column chromatography on silica: packed in CH$_2$Cl$_2$, elution with 1–2% MeOH in CH$_2$Cl$_2$, v/v, and gave the coupled product 107 (2.99 g 70% yield) as a pale yellow foam.

Preparation of Cyclised Nucleoside 108

To a solution of nucleoside 107 (2.9 g, 4.50 mmol) in THF (25 mL) and water (20 mL) was added lithium hydroxide monohydrate (953 mg, 22.70 mmol) and the reaction mixture was stirred at room temperature for 2 hours. The organic solvent was evaporated under reduced pressure and the residue was diluted with CH$_2$Cl$_2$ (150 mL), washed with saturated aqueous NaHCO$_3$ (2×50 mL), dried (Na$_2$SO$_4$) and evaporated under reduced pressure. The remaining yellow foam was purified by column chromatography on silica: packed in CH$_2$Cl$_2$, elution with 0–1% MeOH in CH$_2$Cl$_2$, v/v, affording the cyclised product 108 (1.64 g, 73% yield) as an off-white foam.

$^1$H NMR (400 MHz, CDCl$_3$) δ: 3.06 (3H, s, CH$_3$), 3.91 (1H, d, J7.87, H-1"a), 3.94 (1H, s, H-3'), 4.12 (1H, d, J 8.06, H-1"b), 4.58 (2H, s, CH$_2$), 4.59 (1H, d, J 12.81, H-5'a), 4.67 (1H, s, H-2'), 4.70 (1H, d, J 11.53, H-5'b), 5.67 (1H, s, H-1'), 5.75 (1H, d, J 8.24, H-5), 7.33–7.45 (5H, m, phenylbenzyl), 7.56–7.59 (5H, m, phenylbenzyl, H-6), 9.32 (1H,bs, NH). $^{13}$C NMR (400 MHz, CDCl$_3$) δ: 37.76 (CH$_3$), 63.94 (C-5'), 71.61, 72.10, 76.25, 76.56 (C-2', C-3', C-1", CH$_2$), 85.61, 87.68 (C-1', C-4'), 102.12 (C-5), 126.91, 127.17, 127.36, 128.27, 128.67, 135.24 (Ar), 138.31 (C-6), 140.28, 141.20 (Ar), 149.54 (C-2), 162.94 (C-4).

Preparation of Benzoate 109 and 5'-alcohol 110

Nucleoside 108 (1.56 g, 3.11 mmol) was dissolved in dry N,N-dimethylacetamide (40 mL) under N$_2$, and sodium benzoate (2.25 g, 15.61 mmol) was added. The slurry was heated to 100° C. and stirred at this temperature for 3 hours. The mixture was filtered through a thin pad of Celite™, which was washed with plenty of CH$_2$Cl$_2$. The combined filtrates were diluted with CH$_2$Cl$_2$ (150 mL) and washed with saturated aqueous NaHCO$_3$ (3×50 mL), dried (Na$_2$SO$_4$) and evaporated under reduced pressure. The remaining material was passed through a small column of silica; elution with 0–1% MeOH in CH$_2$Cl$_2$, v/v, affording a clear colourless syrup. This material was dissolved in a minimum amount of hot 96% EtOH, and on cooling a white crystalline product formed, which was isolated by filtration and dried under high vacuum, yielding benzoate 109 (1.41 g, 86%).

An analytical sample of 109 was debenzoylated by treatment with NH$_4$OH in MeOH and gave the 5'-alcohol 110 as a white powder after recrystallisation from EtOH/water (1:1, v/v). $^1$H NMR (400 MHz, DMSO-d$_6$) δ: 3.72 (1H, d, J 7.88, H-1"a), 3.81 (2H, d, J 5.31, H-5'a+b), 3.89 (1H, d, J 7.88, H-1"b), 3.97 (1H, s, H-3'), 4.50 (1H, s, H-2'), 4.66 (2H, s, CH$_2$, phenylbenzyl), 5.31 (1H, t, J 5.50, 5'-OH), 5.51 (1H, s, H-1'), 5.64 (1H, d, J 8.06, H-5), 7.34–7.45 (m, 5H, phenylbenzyl), 7.48–7.67 (m, 4H, phenylbenzyl), 7.76 (1H, d, J 8.24, H-6), 11.38 (1H, s, NH). $^{13}$C NMR (NMR (400 MHz, DMSO-d$_6$) δ: 56.05 (C-5'), 70.89, 71.65, 75.93, 76.56 (C-2', C-3', CH$_2$, C-1"), 86.55, 88.38 (C-1', C-4'), 100.95 (C-5), 126.60, 126.68, 127.46, 128.08, 128.96, 137.15 (Ar), 139.07 (C-6), 139.52, 139.91 (Ar), 150.04 (C-2), 163.37.

Preparation of 3'-alcohol 111 and mono LNA-U 112

To a stirred solution of nucleoside 109 (910 mg, 1.73 mmol) in dry CH$_2$Cl$_2$ (20 mL) under N$_2$ was added anhydrous FeCl$_3$ (Aldrich, 99.99+%, 560 mg, 3.45 mmol). The reaction mixture (initially a clear red-brown solution. After ca. 30 min. a brown precipitate was observed, which changed to green-blue after another 30 min.) was stirred at room temperature for 2.5 hours. The reaction was quenched by addition of water (10 mL) and diluted with CH$_2$Cl$_2$. The mixture was filtrated through a thin pad of Celite™, that was washed with CH$_2$Cl$_2$ and MeOH. The combined filtrates were washed with saturated aqueous NaHCO$_3$ (2×50 mL), dried (Na$_2$SO$_4$) and evaporated under reduced pressure. The residue was purified by column chromatography on silica: packed in 1% MeOH in CH$_2$Cl$_2$, v/v, and eluted with 2–5% MeOH in CH$_2$Cl$_2$, v/v, and gave 3'-alcohol 111 (344 mg, 56% yield) as a white solid material.

An analytical amount of 111 was debenzoylated by treatment with NH$_4$OH in MeOH and gave LNA-U-diol 112 as a white powder after recrystallization from MeOH.

$^1$H NMR (400 MHz, DMSO-d$_6$) δ: 3.62 (1H, d, J 7.87, H-1"a), 3.75 (2H, bd, J4.39, H-5'a+b), 3.83 (1H, d, J 7.87, H-1"b), 3.87 (1H, bd, J 2.75, H-3'), 4.14 (1H, s, H-2'), 5.14 (1H, bt, J4.95, 5'-OH), 5.42 (1H, s, H-1'), 5.62 (1H, d, J 8.06, H-5), 5.66 (1H, bd, J 3.66, 3'-OH), 7.75 (1H, d, J 8.24, H-6), 11.34 (1H, bs, NH).). $^{13}$C NMR (NMR (400 MHz, DMSO-d$_6$) δ: 56.03 (C-5'), 68.71, 71.07, 78.96 (C-2', C-3', C-1"), 86.43, 88.93 (C-1', C-4'), 100.89 (C-5), 139.20 (C-6), 150.04 (C-2), 163.31 (C-4).

EXAMPLE 12

Preparation of Nucleoside 4C

To a stirred suspension of bismesylate 3 (13.0 g, 25.47 mmol) and N$^4$-acetylcytosine (6.24 g, 40.75 mmol) in dry CH$_3$CN (250 mL) under N$_2$ was added N,O-bis (trimethylsilyl)acetamide (25.0 mL, 102.25 mmol, Fluka 97%). The mixture was heated to 40° C. and stirred at this temperature until a clear solution resulted (ca. 20 min.). The mixture was cooled to room temperature and trimethylsilyl triflate (10.0 mL, 55.34 mmol) was added dropwise. The resulting reaction mixture was heated to reflux and stirred at this temperature for 2.5 hours. The mixture was cooled in an ice bath and saturated aqueous NaHCO$_3$ (100 mL) was carefully added. The formed solid material was filtrated off and washed with CH$_2$Cl$_2$ (60 mL). Layers were separated and the aqueous layer was extracted with CH$_2$Cl$_2$ (100 mL). The combined organic layers were diluted with CH$_2$Cl$_2$ (250 mL) and washed with saturated aqueous NaHCO$_3$ (2×100 mL), dried (MgSO$_4$) and evaporated under reduced pressure. The residue (yellow oil) was subjected to column chromatography on silica: packed in 1% MeOH in CH$_2$Cl$_2$, elution with 1–2% MeOH in CH$_2$Cl$_2$, v/v and gave the title compound 4C (9.16 g, 60% yield) as a pale yellow foam.

$^1$H NMR (400 MHz, CDCl$_3$) δ: 2.12 (3H, s, CH$_3$ (Ac)), 2.26 (3H, s, CH$_3$ (Ac)), 3.00 (3H, s, CH$_3$ (Ms)), 3.01 (3H, s, CH$_3$ (Ms)), 4.35–4.80 (8H, m, H-2', H-3', H-1"a+b, H-5'a+b, CH$_2$-benzyl), 5.72–5.73 (2H, m, H-1', H-5), 7.27–7.42 (5H, m, Ar), 7.70 (1H, d, J7.50, H-6), 9.50 (1H, bs, NH). $^{13}$C NMR (400 MHz, CDCl$_3$) δ: 20.66, 24.86 (2×CH$_3$ (Ac)), 37.40, 37.51 (2×CH$_3$ (Ms)), 67.67, 68.05, 73.84, 74.35, 77.89 (C-2', C-3', C-5', C-1", CH$_2$ (Bn)), 84.62 (C-4'), 94.58 (C-1'), 96.88 (C-5), 128.24, 128.27, 128.47, 136.59 (Ar), 146.72 (C-6), 154.25 (C-2'), 163.19 (C-4), 169.75, 170.59 (2×CO).

Preparation of Nucleoside 5C

Nucleoside 4C (5.6 g, 9.28 mmol) was dissolved in THF/H$_2$O (90 mL, 1/1, v/v), and LiOH.H$_2$O (2.34 g, 55.76 mmol) was added. The reaction mixture was stirred at room temperature for 4 hours and the mixture was concentrated under reduced pressure to ca. 50 mL. The residue was partitioned between CH$_2$Cl$_2$ (200 mL) and saturated aqueous NaHCO$_3$ (100 mL). The bright yellow aqueous layer was extracted with CH$_2$Cl$_2$ (2×100 mL). To the combined organic layers, containing precipitated product, was added MeOH until a clear solution was obtained, which was dried (Na$_2$SO$_4$) and evaporated under reduced pressure. The remaining pale yellow solid material was dried under high vacuum and gave 5aC (3.75 g, 95% yield), which was used without further purification. $^1$H NMR (400 MHz, CD$_3$OD) δ: 3.15 (3H, s, CH$_3$ (Ms)), 3.89 (1H, d, J 8.06, H-1"a), 3.92 (1H, s, H-3'), 4.06 (1H, d, J 7.87, H-1"b), 4.52 (1H, s, H-2'), 4.56 (1H, d, J 11.54, CHaHb (Bn)), 4.60 (1H, d, J 2.93, H-5'a), 4.64 (1H, d, J 2.38, H-5'b), 4.67 (1H, d, J 12.08, CHa Hb (Bn)), 5.63 (1H, s, H-1'), 5.89 (1H, d, J 7.51, H-5), 7.28–7.32 (5H, m, Ar), 7.70 (1H, d, J 7.69, H-6). $^{13}$C NMR (400 MHz, CD$_3$OD) δ: 35.53 (CH$_3$ (Ms)), 64.19, 70.97, 71.32, 75.31, 76.25 (C-2', C-3', C-5', C-1", CH$_2$ (Bn)), 84.98 (C-4'), 87.56 (C-1'), 93.88 (C-5), 127.22, 127.32, 127.57, 136.53 (Ar), 139.05 (C-6), 155.61 (C-2), 165.81 (C-4).

Preparation of Benzoate 5aC and 3'-alcohol 6aC

Crude mesylate 5C (3.75 g, 8.86 mmol) was dissolved in dry DMF (100 mL) under N$_2$ and sodium benzoate (3.83 g, 26.58 mmol) and Cs$_2$CO$_3$ (4.33 g, 13.29 mmol) was added. The suspension was heated to 50° C. and stirred at this temperature for 17 hours. The resulting very thick pale yellow slurry was diluted with DMF (100 mL), and more sodium benzoate (2.6 g, 18.04 mmol) was added and the temperature was increased to 65° C. Stirring was continued for 5 hours at this temperature. Then more Cs$_2$CO$_3$ (2.2 g) was added and the mixture was stirred for an additional 2.5 hours. The reaction mixture was cooled to room temperature and concentrated under reduced pressure. The residue was partitioned between CH$_2$Cl$_2$ (250 mL) and saturated aqueous NaHCO$_3$ (250 mL). The aqueous layer was extracted with CH$_2$Cl$_2$ (2×150 mL) and the combined organic layers were washed with brine (100 mL), dried (Na$_2$SO$_4$) and evaporated under reduced pressure. The crude product was purified by column chromatography on silica: packed in 2% MeOH in CH$_2$Cl$_2$, v/v, elution with 2–4% MeOH in CH$_2$Cl$_2$, v/v, and gave benzoate 5aC (3.35 g, 84%) as a pale yellow solid material.

To a stirred solution of nucleoside 5aC (694 mg, 1.54 mmol) in ethanol (15 mL) and cyclohexene (6 mL) was added palladium hydroxide (20% on carbon moist, 174 mg). The mixture was heated to reflux and stirred at this temperature for 6 hours. More palladium hydroxide (87 mg) and cyclohexene (3 mL) was added and stirring continued at reflux for 17 hours. Then more palladium hydroxide (68 mg) and cyclohexene (2 mL) was added and the mixture was stirred for another 2.5 hours. The reaction mixture was cooled to room temperature and the catalyst was removed by filtration through a small pad of Celite™. The solvents were evaporated under reduced pressure and gave the free 3'-alcohol 6aC (416 mg, 75% yield) as a white solid material. $^1$H NMR (400 MHz, CD$_3$OD) δ: 3.96 (1H, d, J 8.97, H-1"a), 4.12 (1H, s, H-3'), 4.13 (1H, d, J 9.00, H-1"b), 4.39 (1H, s, H-2'), 4.73 (1H, d, J 9.83, H-5'a), 4.84 (1H, d, J 9.85, H-5'b), 5.59 (1H, s, H-1'), 5.76 (1H, d, J 7.41, H-5), 7.56–7.72 (3H, m, Ar), 7.75 (1H, d, J 7.45, H-6), 8.07–8.10 (2H, m, Ar). $^{13}$C NMR (400 MHz, CD$_3$OD) δ: 59.27, 69.12, 70.55, 78.80 (C-5', C-3', C-2', C-1"), 85.92, 87.26 (C-1', C-4'), 93.54 (C-5), 128.02, 128.69, 128.98, 132.82 (Ar), 139.04 (C-6), 155.56 (C-2), 165.16 (C-4), 165.74 (CO).

Preparation of Diol 7aC

Nucleoside 6aC (390 mg, 1.08 mmol, crude material), was co-evaporated with dry pyridine (3×) and re-dissolved in dry pyridine (5.0 mL) under N$_2$. Benzoyl chloride (0.25 mL, 2.15 mmol) was added dropwise and the reaction mixture was stirred at room temperature for 60 min. The mixture was cooled in an ice bath and MeOH (20 mL) was added followed by addition of 2 M NaOH (5.0 mL). The reaction mixture was stirred at 0–5° C. for 20 min., then diluted with CH$_2$Cl$_2$ (100 mL) and washed with saturated aqueous NaHCO$_3$ (2×50 mL). The organic layer was dried (Na$_2$SO$_4$) and evaporated under reduced pressure. The residue was subjected to column chromatography on silica: packed in 2% MeOH in CH$_2$Cl$_2$, v/v, elution with 5–7% MeOH/CH$_2$Cl$_2$, v/v, and gave the protected nucleoside 7aC (97 mg, 25% yield) as a white solid material. $^1$H NMR (400 MHz, DMSO-d$_6$) δ: 3.71 (1H, d, J 7.69, H-1"a), 3.79–3.82 (2H, m, H-5'a+b), 3.87–3.89 (2H, m, H-1"b, H-3'), 4.24 (1H, s, H-2'), 5.17 (1H, t, J 5.67, OH), 5.53 (1H, s, H-1'), 5.68 (1H, d, J 7.48, H-5), 7.40–7.65 (3H, m, Ar), 7.99 (2H, d, J 7.33, Ar), 8.25 (1H, d, J 7.51, H-6), 11.26 (1H, bs, NH). $^{13}$C NMR (400 MHz, DMSO-d$_6$) δ: 56.31, 68.53, 71.20, 78.69 (C-1", C-2', C-3', C-5'), 87.50, 89.25 (C-1', C-4'), 96.03 (C-5), 128.52, 132.83 (Ar), 144.31 (C-6), 163.35 (C-4).

EXAMPLE 13

1-(2-O-Acetyl-3-O-benzyl-4-C-methansulfonyloxymethyl-5-O-methanesulfonyl-β-D-ribofuranosyl)-6-N-benzoyladenine (4D)

6-N-Benzoyladenine (11.02 g.; 46.1 mmol) was dried in vacuo overnight. 1,2-Di-O-acetyl-3-O-benzyl-4-C-methanesulfonyloxymethyl-5-O-methanesulfonyl-D-ribofuranose (19.6 g.; 38.4 mmol) (3) was coevaporated in anh. acetonitrile (3×50 mL) and dried in vacuo overnight. 3 was redissolved in anh. 1,2-dichloroethane (stored over molecular sieves) (175 mL), 6-N-Benzoyladenine was added followed by N,O-bistrimethylsilylacetamide (25.1 mL; 101.3 mmol). The mixture was refluxed for 1 h and cooled to rt. TMS-triflate (13.9 mL; 76.8 mmol) was added and the mixture was refluxed for 5 h, stirred overnight at rt, refluxed for further 24 h (red-brown solution) and cooled to rt. The solution was poured into an ice-cold saturated aqueous solution of NaHCO$_3$ (200 mL) and stirred for 0.5 h. The precipitate was filtered off, the phases were separated and the organic phase was washed with a saturated aqueous solution of NaHCO$_3$ (3×150 mL), dried (Na$_2$SO$_4$) and evaporated. Purification by silica gel column chromatography (1–1.5% MeOH in CH$_2$Cl$_2$) gave 4D as a slightly yellow solid in 68% yield (18.0 g.). NMR was consistent with the data reported in an earlier patent.

(1S, 3R, 4R, 7S)-7-Benzyloxy-1-methanesulfonyloxymethyl-3-(6-N-benzoyl-adenine-9-yl)-2,5-dioxabicyclo[2.2.1]heptane (5D)

4D (17.9 g.; 26.1 mmol) was dissolved in THF (160 mL) and water (110 mL). LiOHxH$_2$O (5.5 g.; 131 mmol) was added and the mixture was stirred for 3.5 h at rt. The solution was neutralized with AcOH (~6 mL) to give a precipitate. The precipitate was filtered off and washed with water to give 5D as an off-white solid in 80% yield (11.6 g.). From the mother liquor was additional 5D isolated by filtration as a yellow solid (940 mg.; 6%). $\delta_H$ (DMSO-d$_6$/CDCl$_3$): 8.63 (1H, s), 8.30 (1H, s), 8.04 (2H, m) 7.53–7.42 (3H, m), 7.25–7.21 (5H, m), 6.10 (1H, s), 4.82 (1H, s), 4.67–4.56 (4H, m), 4.41 (1H, s), 4.11 (1H, d, J=7.9 Hz), 3.96 (1H, d, J=8.1 Hz), 3.04 (s, 3H). $\delta_C$ (DMSO-d$_6$/CDCl$_3$): 165.5, 151.5, 150.8, 150.1, 140.6, 136.6, 133.1, 132.0, 128.2, 128.0, 127.9, 127.6, 127.3, 124.5, 86.0, 84.8, 78.1, 76.6, 71.8, 71.7, 64.7, 37.1.

(1S, 3R, 4R, 7S)-7-Benzyloxy-1-benzoyloxymethyl-3-(6-N-benzoyl-adenine-9-yl)-2,5-dioxabicyclo[2.2.1]heptane (28)

(1S, 3R, 4R, 7S)-7-Benzyloxy-1-methanesulfonyloxymethyl-3-(6-N-benzoyl-adenine-9-yl)-2,5-dioxabicyclo-[2.2.1]heptane (5D) (11.5 g.; 20.8 mmol) was dissolved in anh. DMF (450 mL). Sodium benzoate (5.40 g.; 37.4 mmol) was added and the mixture was heated to 90° C. for 7 h. The solution was cooled to rt., filtered, evaporated and coevaporated with AcCN. The residue was redissolved in dichloromethane (150 mL) and a saturated aqueous solution of NaHCO$_3$ (150 mL) was added. The phases were separated and the organic phase was washed with a saturated aqueous solution of NaHCO$_3$ (2×100 mL) and brine (100 mL), dried (Na$_2$SO$_4$) and evaporated to give 12.5 g. of a yellowish solid. Recrystallization from EtOH:H$_2$O (1250 mL; 1:1 v/v) gave 28 in 88% yield (10.63 g.). $\delta_H$ (DMSO-d$_6$): 11.2 (1H, br s), 8.72 (1H, s), 8.48 (1H, s), 8.06 (2H, m), 7.94 (2H, m), 7.66 (2H, m), 7.54 (4H, m), 7.36–7.26 (5H, m), 6.11 (1H, s), 4.97 (1H, s), 4.82 (2H, s), 4.77 (1H, s), 4.75 (1H, d, J=12.4 Hz), 4.69 (1H, d, J=11.9 Hz), 4.19 (1H, d, J=8.0 Hz), 4.07 (1H, d, J=7.9 Hz). $\delta_C$ (DMSO-d$_6$): 165.3, 150.5, 141.9, 137.7, 133.7, 132.5, 129.3, 129.1, 128.9, 128.6, 128.5, 128.3, 127.7, 127.6, 125.7, 85.9, 85.3, 77.9, 77.1, 72.0, 71.3, 60.6.

(1S, 3R, 4R, 7S)-7-Benzyloxy-1-hydroxymethyl-3-(adenin-9-yl)-2,5-dioxabicyclo-[2.2.1]heptane (27)

28 (10.6 g.; 18.4 mmol) was suspended in a mixture of MeOH (125 mL) and ammonium hydroxide (250 mL). The solution was stirred overnight at room temperature and more ammonium hydroxide (100 mL) was added. Additional ammonium hydroxide (50 mL) was added after 7 h and the mixture was stirred overnight. Additional ammonium hydroxide (50 mL) was again added and the mixture was stirred overnight, filtered and dried to give 27 (6.12 g.; 90%) as an off-white solid. $\delta_H$ (DMSO-d$_6$): 8.19 (1H, s), 8.15 (1H, s), 7.33–7.30 (5H, m), 5.97 (1H, s), 5.19 (1H, t), 4.74 (1H, s), 4.63 (2H, s), 4.36 (1H, s), 3.96 (1H, d), 3.83 (3H, m). $\delta_C$ (DMSO-d$_6$): 156.1, 152.8, 148.6, 138.0, 137.9, 128.3, 127.7, 127.6, 119.1, 88.0, 85.4, 77.3, 77.0, 72.1, 71.3, 56.8.

(1S, 3R, 4R, 7S)-7-Hydroxy-1-hydroxymethyl-3-(adenin-9-yl)-2,5-dioxabicyclo-[2.2.1]heptane (30)

27 (6.0 g.; 16.2 mmol) was suspended in MeOH (100 mL). Pd(OH)$_2$-C (2 g) was added followed by ammonium formate (8.2 g; 130 mmol) and the solution was heated to 60° C. After 3 h more catalyst (1 g.) was added followed by ammonium formate (2 g). After further 4 h, the hot solution was filtered through a thin filter paper and washed with boiling MeOH (500 mL). The catalyst was stirred in MeOH (200 mL) overnight and filtered off and was afterwards boiled in MeOH:H$_2$O (200 mL; 1:1 v/v). Evaporation gave 30 (~4 g.; 88%). $\delta_H$ (DMSO-d$_6$): 8.22 (1H, s), 8.15 (1H, s), 7.30 (2H, br s), 5.89 (1H, s), 5.68 (1H, d, J=4.2 Hz), 5.05 (1H, t, J=5.8 Hz), 4.41 (1H, s), 4.25 (1H, d, J=3.7 Hz), 3.92 (1H, d, J=7.8 Hz), 3.82 (2H, m), 3.76 (2H, d, J=7.9 Hz). $\delta_C$ (DMSO-d$_6$): 156.1, 152.8, 148.5, 137.9, 119.1, 88.6, 85.4, 79.3, 71.5, 70.0, 56.8.

(1R, 3R, 4R, 7S)-3-(6-N-Benzoyladenine-9-yl)-1-(4,4'-Dimethoxytrityloxymethyl)-7-Hydroxy-2,5-dioxabicyclo[2.2.1]heptane (31)

30 (~4 g.; 14.3 mmol) was coevaporated several times with anhydrous pyridine. The compound was resuspended in anhydrous pyridine (70 mL). DMTCl (6.78 g.; 20 mmol), NEt$_3$ (2.8 mL; 20 mmol) and DMAP (44 mg.; 0.36 mmol) was added. After 4.5 h. at rt. TMSCl (9.1 mL; 71.5 mmol) was added. After further 45 min. BzCl (8.3 mL; 71.5 mmol) was added and the mixture was stirred overnight, cooled to 0° C. followed by addition of water (18 mL). After 5 min, ammonium hydroxide (25–32% (aq)) (35 mL) was added. The cooling bath was removed and the mixture was stirred for 35 min. and evaporated. The residue was redissolved in dichloromethane (150 mL) and brine (150 mL). The phases were separated and the organic phase was washed with brine (150 mL), dried (Na$_2$SO$_4$) and evaporated. Purification (2 times) by silica gel column chromatography (0.5–2.5% MeOH in CH$_2$Cl$_2$ with 0.5% NEt$_3$) gave 31 as a slightly yellow solid which was dissolved in dichloromethane (5 mL) and precipitated in rapidly vortexing hexanes (400 mL) and filtered. Yield (7.0 g.; 63% from 27). NMR was consistent with earlier reported data (A. A. Koshkin, S. K. Singh, P. Nielsen, V. K. Rajwanshi, R. Kumar, M. Meldgaard, C. E. Olsen and J. Wengel; *Tetrahedron*, 1998, 54, 3607–3630).

EXAMPLE 14

9-(2-O-acetyl-3-O-benzyl-4-C-methanesulfonoxymethyl-5-O-methanesulfonyl-β-D-ribofuranosyl)-hypoxantine (4E)

To a mixture of compound 3 (4.65 g, 9.13 mmol) and hypoxanthine (1.5 g, 10.9 mmol) in anhydrous 1,2-dichloroethane (45 mL) was added BSA (5.3 mL, 21.8 mmol) and the mixture was refluxed for 1 h. Trimethylsilyl triflate (1.8 mL, 10.0 mmol) was added drop-wise, the mixture was refluxed for 6 h and cooled to ambient temperature. Dichloromethane (50 mL) was added, the solution was washed with saturated aqueous NaHCO$_3$ (2×100 mL), dried (Na$_2$SO$_4$), and concentrated under reduced pressure. The residue was purified by column silica gel chromatography (1.4 to 6% of methanol/dichloromethane as eluent) to yield 4.5 g (84%) of white solid material consisted of two isomers (ca. 1:4 ratio by $^1$H-NMR) which was used for next synthesis without additional purification. For compound 4E:

$\delta_H$ (CD$_3$Cl) 12.83 (1H, br s, NH), 8.32, 7.95 (2H, 2×s, 8-H, 2-H), 7.40–7.31 (5H, m, Bn), 6.18 (1H, d, J 3.5, 1'-H), 6.00 (1H, dd, J' 5.9, J" 3.5, 2'-H), 5.03 (1H, d, J 6.0, 3'-H), 4.65 (2H, s), 4.64 (1H, d, J 11.0), 4.47 (1H, d, J 10.6), 4.42 (1H, d, J 10.5), 4.39 (1H, d, J 11.4), 3.03, 2.96 (2×3H, 2 s, methanesulfonyls), 2.11 (3H, s, acetyl). $\delta_C$ (CD$_3$Cl) 169.5 (CH$_3$CO), 158.4 (C-6), 148.0 (C-4), 145.8 (C-2), 139.6 (C-8), 136.4, 128.5, 128.4, 128.3, (Bn), 125.4 (C-5), 87.8, 84.2, 77.6, 74.6, 73.8, 67.6, 67.4 (ribose, Bn), 37.6, 37.4 (methanesulfonyls), 20.5 (acetyl).

(1S, 3R, 4R, 7S)-7-Benzyloxy-1-methanesulfonoxymethyl-3-(hypoxantin-9-yl)-2,5-dioxabicyclo[2.2.1]heptane (21)

To a solution of compound 4E in 1,4-dioxane (80 mL) was added 1M aq. NaOH (80 mL) and the mixture was stirred for 1 h. Acetic acid (20 mL) was added, the solution was concentrated under reduced pressure to ca. half of its volume and cooled in ice-bath. The precipitate formed was filtered off, washed with ice-cold water and dried in vacuo. Yield: 2.4 g (73%) of white solid material consisted of two isomers (ca. 1:10 by $^1$H-NMR) For compound 21:

$\delta_H$ (CD$_3$Cl/DMSO-d$_6$) 12.31 (1H, br s, NH), 7.92, 7.86 (2H, 2×s, 8-H, 2-H), 7.32–7.28 (5H, m, Bn), 6.02 (1H, s, 1'-H), 4.75 (1H, s, 2'-H), 4.65 (2H, s), 4.63 (1H, d, J 7.5), 4.60 (1H, d, J 7.2), 4.31 (1H, s, 3'-H), 4.18 (1H, d, J 8.1), 4.01 (1H, d, J 8.1), 3.08 (3H, 2 s, methanesulfonyl). $\delta_C$ (CD$_3$Cl/DMSO-d$_6$) 156.7 (C-6), 146.6 (C-4), 144.9 (C-2), 136.4, 136.3, 127.9, 127.6, 127.3, (C-8, Bn), 125.0 (C-5), 85 9, 84.7, 77.0, 76.7, 71.8, 71.7, 64.5 (ribose, Bn), 37.1, (methanesulfonyl).

(1S, 3R, 4R, 7S)-1-Benzoyloxymethyl-7-benzyloxy-3-(hypoxantin-9-yl)-2,5-dioxabicyclo[2.2.1]heptane (22)

A mixture of compound 21 (two isomers; 1.95 g, 4.36 mmol) and sodium benzoate (0.94 g, 6.54 mmol) in anhydrous DMF (100 mL) was stirred at 80° C. for 24 h. The solution was cooled to room temperature, filtrated and concentrated to an oil. The residue was separated by column silica gel chromatography (2 to 3.5% methanol/dichloromethane as eluent) to give 1.51 g (73%) of compound 22 as a white solid material.

$\delta_H$ (CD$_3$Cl) 13.08 (1H, br s, NH), 8.23, (1H, s 8-H), 7.98 (2H, m, Bz), 7.89 (1H, s, 2-H), 7.60 (1H, m, Bz), 7.46 (2H, m, Bz), 7.25–7 23 (5H, m, Bn), 6.05 (1H, s, 1'-H), 4.83 (1H, s, 2'-H), 4.80 (1H, d, J 12.6), 4.68 (1H, d, J 11.9), 4.67 (1H, d, J 12.8), 4.57 (1H, d, J 11.7), 4.28 (1H, d, J 8.2), 4.27 (1H, s, 3'-H), 4.10 (1H, d, J 7.9). $\delta_C$ (CD$_3$Cl) 165.7 (Bz), 158.8 (C-6), 147.6 (C-4), 145.3 (C-2), 137.2 (C-8), 136.4, 133.4, 129.4, 129.0, 128.5, 128.4, 128.1, 127.7 (Bz, Bn), 125.1 (C-5), 86.6, 85.8, 77.1, 77.0, 72.5, 72.4, 59.6 (ribose, Bn).

(1S, 3R, 4R, 7S)-7-Benzyloxy-1-hydroxymethyl-3-(hypoxantin-9-yl)-2,5-dioxabicyclo[2.2.1]heptane (23)

To a solution of compound 22 in methanol (20 mL) was added 2M NaOH (2 mL) and 15 min later acetic acid (2 mL). The mixture was cooled in ice-bath, the precipitate was filtered off, washed with water and dried in vacuo. Yield: 0.69 g (85%) of compound 23 as a white solid material.

$\delta_H$ (DMSO-d$_6$) 8.16, (1H, s 8-H), 8.06 (1H, s, 2-H), 7.30–7.20 (5H, m, Bn), 5.95 (1H, s, 1'-H), 4 69 (1H, s, 2'-H), 4.63 (2H, s, Bn), 4.28 (1H, s, 3'-H), 3.95 (1H, d, J 7.7), 3.83 (3H, m). $\delta_C$ (DMSO-d$_6$) 156.6 (C-6), 147.3 (C-4), 146.1 (C-2), 137.9 (C-8), 137.3, 128.3, 127.6, 127.5 (Bn), 124.5 (C-5), 88.2, 85.4, 77.0, 72.1, 71.3, 56.7 (ribose, Bn).

(1R, 3R, 4R, 7S)-1-(4,4'-Dimethoxytrityloxymethyl)-7-benzyloxy-3-(hypoxantin-9 -yl)-2,5-dioxabicyclo[2.2.1] heptane (24)

DMT-chloride (0.7 g, 2.07 mmol) was added to a suspension of compound 23 in anhydrous pyridine and the mixture was stirred at 80° C. (oil bath) for 2 h. The solution was diluted with ethyl acetate (150 mL), washed with NaHCO$_3$ (200 mL), water (2×200 mL), dried (Na$_2$SO$_4$) and concentrated under reduced pressure. The residue was purified by silica gel HPLC (1 to 4% of methanol/dichloromethane containing 0.5% of pyridine) to yield 1.02 g (92%) of compound 24 as a white solid material.

$\delta_H$ (CD$_3$Cl) 13.15 (1H, br s, NH), 8.23, (1H, s 8-H), 8.15 (1H, s, 2-H), 7.45 (m, 2H, DMT), 7.36–7.12 (12H, m, Bn, DMT), 6.86–6.80 (m, 4H, DMT), 6.07 (1H, s, 1'-H), 4.71 (1H, s, 2'-H), 4.56 (1H, d, J 11.7, Bn), 4.61 (1H, d, J 11.7, Bn), 4.32 (1H, s, 3'-H), 4.03 3.95 (1H, d, J 7.8), 3.95 (1H, d, J 7.8), 3.78, 3.77 (6H, 2×s, DMT), 3.58 (1H, d, J 10.9), 3.45 (1H, d, J 11.0). $\delta_C$ (CD$_3$Cl) 159.1, 158.5, 147.6, 145.1, 144.2, 137.5, 136.7, 135.3, 135.2, 129.9, 129.8, 128.9, 128.3, 128.1, 127.9, 127.6, 126.9, 125.2, 113.2 (DMT, Bn, hypoxantine), 87.3, 86.6, 86.4, 77.2, 72.8, 72.2, 58.4 (ribose, Bn), 55.1 (DMT).

(1R, 3R, 4R, 7S)-1-(4,4'-Dimethoxytrityloxymethyl)-7-hydroxy-3-(hypoxantin-9-yl)-2,5-dioxabicyclo[2.2.1] heptane (25)

Sodium formate (1.2 g) was added to a mixture of compound 24 (1.02 g, 0.52 mmol) and Pd/C (10%, 0.5 g) in methanol (20 mL). The mixture was refluxed for 20 min, cooled to room temperature and diluted with dichloromethane (20 mL). The catalyst was filtered off and the filtrate was concentrated under reduced pressure to give a white solid material, which was crystallised from 50% ethanol/water to yield 680 mg (77%) of compound 25.

$\delta_H$ (DMSO-d$_6$) 8.12, (1H, s 8-H), 8.09 (1H, s, 2-H), 7.43–7.24 (m, 9H, DMT), 6.90 (m, 4H, DMT), 5 97 (1H, s, 1'-H), 4.44 (1H, s, 2'-H), 4.33 (1H, s, 3'-H), 3.97 (1H, d, J 7.5, Bn), 3.91(1H, d, J 7.7), 3.74 (6H, s, DMT), 3 55 (1H, d, J 10.6). $\delta_C$ (DMSO-d$_6$) 158.2, 156.6, 147.3, 146.1, 144.8, 137.1, 135.5, 135.3, 129.8, 127 9, 127.7, 126.8, 124.6, 113.3 (DMT, hypoxantine), 87.1, 85.6, 79.3, 71.8, 70.5, 59.9 (ribose), 55.1 (DMT).

(1S, 3R, 4R, 7S)-1-Benzoyloxymethyl 7-benzyloxy--3-(6-chloropurin-9-yl)-2,5-dioxabicyclo[2.2.1]heptane (26)

Thionyl chloride (2.1 mL, 29 mmol) and DMF (1 mL) were added to a solution of compound 22 (1.24 g, 2.62 mmol) in dichloromethane. The mixture was stirred at 30° C. (oil bath) overnight, diluted with ethyl acetate (50 mL), washed with NaHCO$_3$ (sat. aq., 100 mL) and water (2×50 mL), dried (Na$_2$SO$_4$), and concentrated under reduced pressure. A white solid residue was purified by column silica gel chromatography using 0 to 2% of methanol/dichloromethane as eluent. Yield: 1.2 g (93%) of compound 26 as a white solid material.

$\delta_H$ (CD3Cl) 8.69 (1H, s, 8-H), 8.16 (1H, s, 2-H), 7.95 (2H, m, Bz), 7.62 (1H, m, Bz), 7.46 (2H, m, Bz), 7.25–7.20 (5H, m, Bn), 6.11 (1H, s, 1'-H), 4.93 (1H, s, 2'-H), 4.82 (1H, d, J 12.7), 4.68 (1H, d, J 11.9), 4.65 (1H, d, J 12.7), 4.57 (1H, d, J 11.9), 4.31 (1H, J 8.0), 4.26 (1H, s, 3'-H), 4.12 (1H, d, J8.0). $\delta_C$ (CD$_3$Cl) 165.7 (Bz), 152.0, 151.3, 150.1, 142.4, 136.2, 133.5, 132.0, 129.4, 129.0, 128.5, 128.4, 128.2, 127.7, 86.9, 86.0, 77.1, 76.7, 72.6, 72.4, 59.5.

(1S, 3R, 4R, 7S)-7-Benzyloxy-1-hydroxymethyl-3-(adenin-9-yl)-2,5-dioxabicyclo[2.2.1]heptane (27)

32% NH$_4$OH (20 mL) was added to a solution of compound 26 (1.2 g, 2.43 mmol) in THF (20 mL) and the mixture was stirred for 48 h at ambient temperature. The solvents were partly removed under reduced pressure (ca. ½ of volume) and the solution was cooled in an ice-bath. The precipitate was collected and re-crystallised from water to yield compound 27 (450 mg, 50.3%) as a white solid material.

$\delta_H$ (DMSO-d$_6$) 8.17, (1H, s 8-H), 8.13 (1H, s, 2-H), 7.30–7.20 (5H, m, Bn), 5.95 (1H, s, 1'-H), 5.15 (1H, t, J 5.1, 5'-OH), 4.72 (1H, s, 2'-H), 4.61 (2H, s, Bn), 4.34 (1H, s, 3'-H), 3.94 (1H, d, J 7.7), 3.81 (3H, m). $\delta_C$ (DMSO-d$_6$) 156.0 (C-6), 152.7 (C-4), 148.6 (C-2), 137.9 (C-8), 128.2, 127.6, 127.5 (Bn), 119.0 (C-5), 88.0, 85.3, 77.2, 77.0, 72.0, 71.2, 56.8 (ribose, Bn).

What is claimed is:

1. A method for the synthesis of a compound of the formula II:

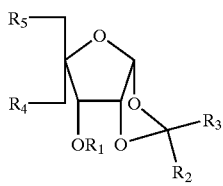

wherein $R_1$ is selected from optionally substituted aryl($C_{1-6}$-alkyl), optionally substituted tetrahydropyran-2-yl, optionally substituted arylcarbonyl and optionally substituted aryl;
each of the substituents $R_2$ and $R_3$ is independently selected from hydrogen, optionally substituted $C_{1-6}$alkyl, optionally substituted aryl, and optionally substituted aryl($C_{1-6}$-alkyl), or $R_2$ and $R_3$ together designate $C_{3-7}$-alkylene, with the proviso that $R_2$ and $R_3$ are not both hydrogen;
$R_4$ is $R^{III}SO_2O$— wherein $R^{III}$ is selected from optionally substituted alkyl and optionally substituted aryl; $R_5$ is $R^{IV}SO_2O$— wherein $R^{IV}$ is selected from optionally substituted alkyl and optionally substituted aryl; and provided that $R_4$ and $R_5$ are different;
said method comprising the following step:
treatment of a compound of the formula I:

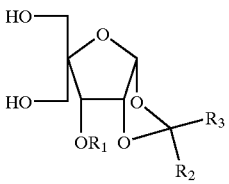

wherein $R_1$ is selected from optionally substituted aryl($C_{1-6}$-alkyl), optionally substituted tetrahydropyran-2-yl, optionally substituted arylcarbonyl and optionally substituted aryl;
each of the substituents $R_2$ and $R_3$ is independently selected from hydrogen, optionally substituted $C_{1-6}$-alkyl, optionally substituted aryl, and optionally substituted aryl($C_{1-6}$-alkyl), or $R_2$ and $R_3$ together designate $C_{3-7}$-alkylene, with the proviso that $R_2$ and $R_3$ are not both hydrogen; and
wherein compound I is subsequently treated with two different sulfonyl halides, $R^{III}SO_2X$ and $R^{IV}SO_2X$, wherein $R^{III}$ and $R^{IV}$ are as defined above, and X is a halogen.

2. A method according to claim 1, wherein compound I is first treated with $R^{III}SO_2X$ in a ratio of 1:1–1:1.5 to provide a compound of the formula:

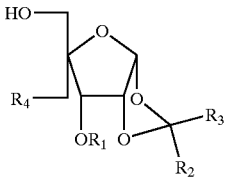

wherein $R_4$ is $R^{III}SO_2O$— and subsequently, the formed compound is treated with $R^{IV}SO_2X$ in a ratio of 1:1–1:2.5, to provide compound II wherein $R_4$ is $R^{III}SO_2O$— and $R_5$ is $R^{IV}SO_2O$—.

3. A method according to claim 1, wherein the treatment of compound I with the two sulfonyl halides is performed in the presence of a base selected from the group consisting of pyridine, 4-dimethylaminopyridine, triethylamine, and sodium hydride.

4. A method according to claim 1, wherein the treatment of compound I with the two sulfonyl halides is performed in the presence of pyridine or 4-dimethylaminopyridine.

5. A method according to claim 1, wherein the treatment of compound I with the two sulfonyl halides is performed in the presence of pyridine.

6. A method according to claim 1, wherein the treatment of compound I with the two sulfonyl halides is performed in the presence of a solvent selected from pyridine, tetrahydrofuran, toluene, xylene, benzene, ether, ethylacetate, acetonitrile, triethylamine, N,N-dimethylformamide, dimethylsulfoxide, dichloromethane, and 1,2-dichloroethane.

7. A method according to any one of claims 3–6, wherein the base and the solvent is the same substance.

8. A method according to claim 1, wherein the treatment of compound I with the two sulfonyl halides is performed at −30° C. to 40° C.

9. A method according to claim 1, wherein the treatment of compound I with the two sulfonyl halides is performed at −5° C. to 30° C.

10. A method according to claim 1, wherein the treatment of compound I with the two sulfonyl halides is performed at 0° C. to 25° C.

11. A method according to claim 1, wherein $R_1$ is selected from the group consisting of benzyl, ortho-, meta-, and para-methylbenzyl, 2-chlorobenzyl, 4-phenylbenzyl, tetrahydropyran-2-yl, benzoyl and phenyl.

12. A method according to claim 1, wherein each of the substituents $R_2$ and $R_3$ independently represent hydrogen, methyl, trifluoromethyl, ethyl, propyl, iso-propyl, butyl, t-butyl, pentyl, cyclopentyl, hexyl, cyclohexyl, phenyl, benzyl, phenylethyl, ortho-, meta-, or para-methylbenzyl, or 2-chlorobenzyl, or $R_2$ and $R_3$ together designate 1,5-pentylene.

13. A method according to claim 1, wherein R' is selected from the group consisting of methyl, trifluoromethyl, ethyl, 2,2,2-trifluoroethyl, propyl, iso-propyl, butyl, nonafluorobutyl, pentyl, cyclopentyl, hexyl, cyclohexyl, benzyl, ortho-, meta- and para-methylbenzyl, 2-chlorobenzyl, phenyl, ortho-, meta-, and para-bromophenyl, and para-nitrophenyl, and X is a halogen.

14. A method according to claim 1, wherein $R^{III}SO_2X$ and $R^{IV}SO_2X$ are each selected from the group consisting of methanesulfonyl chloride, trifluoromethanesulfonyl chloride, ethanesulfonyl chloride, 2,2,2-trifluroethanesulfonyl chloride, nonafluorobutanesulfonyl chloride, α-toluenesulfonyl chloride and para-toluenesulfonyl chloride.

15. A method according to claim 1, wherein either $R^{III}SO_2X$ or $R^{IV}SO_2X$ is methanesulfonyl chloride.

* * * * *